US009725483B2

(12) United States Patent
García Antón et al.

(10) Patent No.: US 9,725,483 B2
(45) Date of Patent: Aug. 8, 2017

(54) COMPOUNDS FOR THE TREATMENT AND/OR CARE OF THE SKIN AND/OR MUCOUS MEMBRANES AND THEIR USE IN COSMETIC OR PHARMACEUTICAL COMPOSITIONS

(71) Applicant: LUBRIZOL ADVANCED MATERIALS, INC., Cleveland, OH (US)

(72) Inventors: José María García Antón, Barcelona (ES); Antonio Vicente Ferrer Montiel, Alicante (ES); Cristina Carreño Serraïma, Barcelona (ES); Raquel Delgado González, Barcelona (ES); Juan Cebrián Puche, Barcelona (ES)

(73) Assignee: LIPOTEC, S.A., Gava (ES)

( * ) Notice: Subject to any disclaimer, the term of this patent is extended or adjusted under 35 U.S.C. 154(b) by 0 days.

(21) Appl. No.: 14/391,472

(22) PCT Filed: Apr. 16, 2013

(86) PCT No.: PCT/EP2013/057939
§ 371 (c)(1),
(2) Date: Oct. 9, 2014

(87) PCT Pub. No.: WO2013/156493
PCT Pub. Date: Oct. 24, 2013

(65) Prior Publication Data
US 2015/0104485 A1    Apr. 16, 2015

Related U.S. Application Data

(60) Provisional application No. 61/624,653, filed on Apr. 16, 2012.

(30) Foreign Application Priority Data

Apr. 16, 2012  (ES) .................................. 201230567

(51) Int. Cl.
| | |
|---|---|
| *C07K 7/06* | (2006.01) |
| *C07K 5/103* | (2006.01) |
| *C07K 5/083* | (2006.01) |
| *A61K 38/00* | (2006.01) |
| *A61K 9/00* | (2006.01) |
| *A61K 9/06* | (2006.01) |
| *A61K 8/64* | (2006.01) |
| *A61Q 19/02* | (2006.01) |
| *A61Q 19/08* | (2006.01) |
| *A61K 38/08* | (2006.01) |
| *A61K 45/06* | (2006.01) |
| *C07K 1/02* | (2006.01) |
| *A61Q 1/04* | (2006.01) |
| *A61Q 1/06* | (2006.01) |
| *A61Q 1/10* | (2006.01) |
| *A61Q 1/14* | (2006.01) |
| *A61Q 15/00* | (2006.01) |
| *A61Q 17/04* | (2006.01) |
| *A61Q 19/00* | (2006.01) |
| *A61Q 19/10* | (2006.01) |

(52) U.S. Cl.
CPC .................. *C07K 7/06* (2013.01); *A61K 8/64* (2013.01); *A61K 9/0014* (2013.01); *A61K 9/06* (2013.01); *A61K 38/005* (2013.01); *A61K 38/08* (2013.01); *A61K 45/06* (2013.01); *A61Q 19/02* (2013.01); *A61Q 19/08* (2013.01); *C07K 1/02* (2013.01); *C07K 5/0804* (2013.01); *C07K 5/1005* (2013.01); *C07K 5/1008* (2013.01); *A61Q 1/04* (2013.01); *A61Q 1/06* (2013.01); *A61Q 1/10* (2013.01); *A61Q 1/14* (2013.01); *A61Q 15/00* (2013.01); *A61Q 17/04* (2013.01); *A61Q 19/001* (2013.01); *A61Q 19/10* (2013.01)

(58) Field of Classification Search
None
See application file for complete search history.

(56) References Cited

U.S. PATENT DOCUMENTS

| 9,333,152 B2* | 5/2016 | Ferrer Montiel | ...... A61K 38/08 |
| 2009/0280140 A1* | 11/2009 | Laal | ...... C07K 14/36 |
| | | | 424/190.1 |

(Continued)

FOREIGN PATENT DOCUMENTS

| WO | WO 2007/015918 A2 | 2/2007 |
| WO | WO 2007/104062 A2 | 9/2007 |
| WO | WO 2011/057163 A2 | 5/2011 |

OTHER PUBLICATIONS

SEQ ID No. 192250 retrieved from http://seqdata.uspto.gov/?pageRequest=docDetail&DocID=US20130330335A1 on Jan. 26, 2016, 2 pages.*
Uniprot database search of ATNT, run Dec. 2, 2015, 14 pages.*
Blast search of SVRVAV retrieved from http://blast.ncbi.nlm.nih.gov/Blast.cgi on Jan. 26, 2016, 12 pages.*
Woolery-Lloyd, et al., "Acne and Rosacea in Skin of Color," Cosmetic Dermatology, vol. 24, No. 4, pp. 159-162 (2011).

(Continued)

*Primary Examiner* — Karlheinz R Skowronek
*Assistant Examiner* — Ronald Niebauer
(74) *Attorney, Agent, or Firm* — Fay Sharpe LLP

(57) ABSTRACT

Compounds of general formula (I): $R_i-W_n-X_m-AA_1-AA_2-AA_3-AA_4-AA_5-AA_6-Y_p-Z_q-R_2$ (I) their stereoisomers, mixtures thereof and/or their cosmetically or pharmaceutically acceptable salts, preparation processes, cosmetic and/or pharmaceutical compositions which contain them and their use in medicine, particularly in the treatment and/or prevention of pain, inflammation, itching, pigmentation disorders and angiogenic skin disorders, and in processes of treatment and/or care of the skin and/or mucous membranes.

15 Claims, No Drawings

(56) References Cited

U.S. PATENT DOCUMENTS

| | | | |
|---|---|---|---|
| 2011/0086806 A1* | 4/2011 | Kretz-Rommel | C07K 14/4726 514/19.3 |
| 2013/0143757 A1* | 6/2013 | Zhong | G01N 33/6893 506/9 |
| 2013/0330335 A1* | 12/2013 | Bremel | G06F 19/18 424/134.1 |

OTHER PUBLICATIONS

Paliouras, et al., "The kallikrein world: an update on the human tissue Kallikreins," Biol. Chem., vol. 387, pp. 643-652 (2006).
Eissa, et al., "Human tissue kallikreins as promiscuous modulators of homeostatic skin barrier functions," Biol. Chem., vol. 389, pp. 669-680 (2008).
Yamasaki, et al., "Kallikrein-mediated proteolysis regulates the antimicrobial effects of cathelicidins in skin," the FASEB J., vol. 20, pp. 2068-2080 (2006).
Yamasaki, et al., "TLR2 Expression is Increased in Rosacea and Stimulates Enhanced Serine Protease Production by Keratinocytes," J. Invest. Dermatol., vol. 130, No. 5, pp. 1297-1306 (2010).
Pistolic, et al., "Host defence peptide LL-37 induces IL-6 expression in human bronchial epithelial cells by activation of the NF-kappaB signaling pathway," J. Innat. Immun. vol. 1, No. 3, pp. 254-267 (2009).
Park, et al., "Collagen synthesis is suppressed in dermal fibroblasts by the human antimicrobial peptide LL-37," J. Invest. Dermatol., vol. 129, pp. 843-850 (2009).
Dooley, "Recent advances in cutaneous melanoma oncogenesis research," Onco. Res., vol. 6, pp. 1-9 (1994).
IUPAC-IUB Commission of Biochemical Nomenclature specified in Eur. J. Biochem., vol. 138, pp. 9-37 (1984).
Roberts, et al., "Unusual amino acids in peptide synthesis," The Peptides, vol. 5, Chapter 6, pp. 341-449 (1983).
Berge, et al., "Pharmaceutical Salts," J. Pharm. Sci., vol. 66, pp. 1-19 (1977).
Stewart, et al., Solid Phase Peptide Synthesis, 2$^{nd}$ Edition, Pierce Chemical Company, pp. 1-95 (1984).
Bodansky, et al., "The Practice of Peptide Synthesis," 2$^{nd}$ Edition, Springer Verlag, Berlin, pp. 77-126 (1994).
Lloyd-Williams, et al., "Chemical Approaches to the Synthesis of Peptides and Proteins," CRC, Boca Raton, FL pp. 1-93 (1997).
Kullman, "Proteases as catalysts for enzymic syntheses of opioid peptides," J. Biol. Chem., vol. 255, No. 17, pp. 8234-8238 (1980).
Lloyd-Williams, "Convergent Solid-Phase Peptide Synthesis," Tetrahedon Report No. 347, vol. 49, No. 48, pp. 11065-11133 (1993).
Atherton, et al., "Solid Phase Peptide Synthesis: A practical approach," IRL Oxford University Press, pp. 1-9, 16-21, and 47-61 (1989).
Matsueda, et al., A p-methylbenzhydrylamine resin for improved solid-phase synthesis of peptide amides, Peptides, vol. 2, pp. 45-50 (1981).
Barlos, et al., "Darstellung geschützter Peptid-Fragmente unter Einsatz substituierter Triphenylmethyl-Harze," Tetrahedron Lett., 30, pp. 3943-3946 (1989). English Summary only.
Barlos et al., "Veresterung von partiell geschützten Peptid-Fragmenten mit Harzen. Einsatz von 2-Chlorotritylchlorid zur Synthese von Leu$^{15}$-Gastrin I", Tetrahedron Lett., 30, pp. 3947-3951 (1989). English Abstract only.
Albericio, et al., "Preparation and application of the 5-(4-(9-fluorenylmethyloxycarbonyl) aminomethyl-3,5-dimethoxyphenoxy)valeric acid (PAL) handle for the solid-phase synthesis of C-terminal peptide amides under mild conditions," J. Org. Chem., vol. 55, pp. 3730-3743 (1990).
Rink, "Solid-phase synthesis of protected peptide fragments using a trialkoxy-diphenyl-methylester resin," Tetrahedron Lett., vol. 28, pp. 3787-3790 (1987).
Wang, "p-Alkoxybenzyl Alcohol Resin and p-Alkoxybenzyloxycarbonylhydrazide Resin for Solid Phase Synthesis of Protected Peptide Fragments," J. Am. Chem. Soc., vol. 95(4), pp. 1328-1333 (1973).
Wilkinson, "Harry's Cosmeticology," Seventh Edition, Longman House, Essex, GB, pp. 50-73 and 757-799 (1982).
Schaab, "Impregnating Fabrics with Microcapsules," HAPPI, pp. 84-86 (1986).
Nelson, "Application of microencapsulation in textiles," Int. J. Pharm, vol. 242, No. 1-2, pp. 55-62 (2002).
Elsner, "Antimicrobials and the Skin Physiological and Pathological Flora," in Hipler, et al., Biofunctional textiles and the Skin, Curr. Probl. Dermatol., vol. 33, pp. 35-41 (2006).
Malcolm, "Controlled release of a model antibacterial drug from a novel self-lubricating silicone biomaterial," J. Cont. Release, vol. 97, No. 2 pp. 313-320 (2004).
Gottschalck, et al. eds., CTFA International Cosmetic Ingredient Dictionary and Handbook, 12$^{th}$ Edition, vol. 3, pp. 3040-3065 (2008).
Kaiser, et al., "Color Test for Detection of Free Terminal Amino Groups in the Solid-Phase Synthesis of Peptides," Anal. Biol. vol. 34, pp. 595-598 (1979).
Christensen, "A Qualitative test for Monitoring Coupling Completeness in Solid Phase Peptide Synthesis Using Chloranil," Acta Chemica Scandinavica, vol. B33, pp. 763-766 (1979).
Reinholz et al., "Chathelicidin LL-37: An Antimicrobial Peptide with a Role in Inflammatory Skin Disease," Annals of Dermatology, vol. 24, No. 2, pp. 126-135 (2012).
Nilsson, et al., "The human cationic antimicrobial protein (hCAP18), a peptide antibiotic, is widely expressed in human squamous epithelia and colocalizes with interleukin-6," Infection and Immunity, American Soc. for Macrobiology, vol. 67, No. 5, pp. 2561-2566 (1999).
International Search Report for PCT/EP2013/057939 dated Jun. 19, 2013.

* cited by examiner

```
SEQUENCE LISTING

<160> NUMBER OF SEQ ID NOS: 42

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(2)
<223> OTHER INFORMATION: Xaa is an amino acid or absent
<220> FEATURE:
<221> NAME/KEY: VARIANT
<222> LOCATION: (3)..(3)
<223> OTHER INFORMATION: Xaa is S or absent
<220> FEATURE:
<221> NAME/KEY: VARIANT
<222> LOCATION: (4)..(4)
<223> OTHER INFORMATION: Xaa is V or A
<220> FEATURE:
<221> NAME/KEY: VARIANT
<222> LOCATION: (5)..(5)
<223> OTHER INFORMATION: Xaa is R or T
<220> FEATURE:
<221> NAME/KEY: VARIANT
<222> LOCATION: (6)..(6)
<223> OTHER INFORMATION: Xaa is V or N
<220> FEATURE:
<221> NAME/KEY: VARIANT
<222> LOCATION: (7)..(7)
<223> OTHER INFORMATION: Xaa is A or T
<220> FEATURE:
<221> NAME/KEY: VARIANT
<222> LOCATION: (8)..(8)
<223> OTHER INFORMATION: Xaa is V or absent
<220> FEATURE:
<221> NAME/KEY: VARIANT
<222> LOCATION: (9)..(10)
<223> OTHER INFORMATION: Xaa is an amino acid or absent

<400> SEQUENCE: 1

Xaa Xaa Xaa Xaa Xaa Xaa Xaa Xaa Xaa Xaa
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Ser Val Arg Val Ala Val
1               5

<210> SEQ ID NO 3
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 3

Ser Ala Arg Val Ala Val
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ser Val Thr Val Ala Val
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Val Arg Asn Ala Val
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Val Arg Val Thr Val
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Ser Ala Thr Val Ala Val
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ser Ala Arg Asn Ala Val
1               5

<210> SEQ ID NO 9
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 9

Ser Ala Arg Val Thr Val
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ser Val Thr Asn Ala Val
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Ala Arg Asn Thr
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Ala Thr Val Thr
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Ala Thr Asn Ala
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Val Thr Asn Thr
1

<210> SEQ ID NO 15
<211> LENGTH: 4
<212> TYPE: PRT
<213> ORGANISM: Artificial Sequence
<220> FEATURE:
```

<223> OTHER INFORMATION: Synthetic peptide

<400> SEQUENCE: 15

Ala Arg Asn Ala
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Ala Thr Asn Thr
1

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Ser Val Thr Val Ala Val Ala Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Ile Ile Ser Ala Arg Val Ala Val
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Ser Ala Arg Val Ala Val Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Leu Ser Val Thr Val Ala Val
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Gly Ala Ala Thr Asn Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Gly Val Ala Arg Asn Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Ser Ala Thr Asn Thr Val
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Val Ser Val Arg Val Ala Val
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Ser Ala Thr Asn Thr Val Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Val Ser Val Arg Val Ala Val Ala
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide

```
<400> SEQUENCE: 27

Ser Ala Thr Asn Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Ser Val Arg Val Ala
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Val Arg Asn Thr
1

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide

<400> SEQUENCE: 30

Val Thr Asn Ala
1

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Ser Ala Arg Val Ala Val Arg Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Ser Val Arg Val Ala Val
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33
```

```
Val Thr Asn Thr Gln Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide

<400> SEQUENCE: 34

Gln Asp Phe His Asp Ile Met Ala
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Ala Thr Asn Ala Val
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Ile Ser Val Thr Val Ala Val
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Ser Ala Arg Asn Thr
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Ser Ala Thr Val Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39
```

```
Ser Ala Thr Asn Ala
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 40

Ala Arg Asn Thr Val
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 41

Ala Thr Val Thr Val
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 42

Ala Thr Asn Ala Val
1               5
```

COMPOUNDS FOR THE TREATMENT AND/OR CARE OF THE SKIN AND/OR MUCOUS MEMBRANES AND THEIR USE IN COSMETIC OR PHARMACEUTICAL COMPOSITIONS

This application claims the benefit of PCT/EP2013/057939, filed Apr. 16, 2013, and ES 201230567, filed Apr. 16, 2012, and U.S. Provisional Application Ser. No. 61/624,653, filed Apr. 16, 2012, from which the PCT application claims priority, the disclosures of all of which are incorporated herein by reference in their entireties.

FIELD OF THE INVENTION

This invention relates to synthetic compounds that present significant effectiveness in the treatment and/or care of the skin and/or mucous membranes, and in particular they useful in the treatment and/or care of those conditions, disorders and/or diseases that improve or are prevented by the inhibition of cytokine release, the inhibition of matrix metalloproteinase activity and/or inhibition of melanogenesis.

BACKGROUND OF THE INVENTION

Skin is formed by three layers: stratum corneum, dermis and epidermis. The stratum corneum is the outermost layer and is formed by corneocytes and lipids which protect the skin from the external environment. The epidermis is composed of keratinocytes, melanocytes and Langerhans cells. The main cell population in the epidermis is keratinocytes, which form a keratinized layer that continually renews itself. Their function is to protect against external agents, whether these be physical, chemical or pathogens. The dermis is located deeper in the skin and is joined to the epidermis by means of the basal membrane. It is formed by fibroblasts, adipocytes and macrophages; it is irrigated by blood vessels and presents numerous nerve endings responsible for transmitting sensations of touch and temperature. Hair follicles as well as sweat, sebaceous and apocrine glands are located in the dermis, and their function is to maintain the integrity and elasticity of the skin.

During aging, a progressive decrease in the functions of the skin is observed giving rise, among other things, to the appearance of the heterogeneity of the skin. Thus the skin suffers changes through aging and this gradually affects its appearance showing redness, changes to the pigmentation, loss of firmness and/or the appearance of wrinkles. The continual exposure to ultraviolet radiation (UV) intensifies these changes, favoring their appearance before maturity is reached. In some individuals even disorders and/or diseases related to excessive redness or marks on the skin develop. There is, therefore, a need to develop new compounds capable of improving the appearance of the skin, standardizing its color, reducing wrinkles and improving firmness.

Redness

One of the cutaneous disorders with redness blamed as a clinical symptom that presents a higher rate of occurrence in the Caucasian race is rosacea. Rosacea is a chronic disorder or disease of the skin that is quite common, it usually appears between the ages of 3 and 50, more in women than men and particularly in Caucasian people with very pale skin. Rosacea affects the central areas of the face and is characterized by recurring episodes of itchiness, reddening, erythemas, papules, pustules, vasodilatation, telangiectasias, pain and inflammation. The symptoms of rosacea are exacerbated by exposure to sun, heat, high humidity, sweat, physical exercise, emotional stress, alcohol intake and spicy food. Furthermore, people with rosacea usually suffer from very dry skin, even presenting desquamation of the skin.

The cause of rosacea is not well established. Until recently, it was thought that the cause was some type of infectious agent, therefore antibiotics were prescribed for its treatment; however, treatments with antibiotics only provide a partial improvement. To treat rosacea and prevent abnormalities in the skin's pigmentation due to associated inflammation, antibiotics have been described such as tetracyclines, dapsone and metronidazoles. [Woolery-Lloyd H. et al. "*Acne and Rosacea in Skin of Color*", Cosmetic Dermatology, (2011), 24:4, 159-162].

Recently, it has been proposed that bradykinin, a local hormone, could have a vasodilatory effect, thus increasing vascular permeability and inflammation. The group of bradykinins is produced due to kininogen hydrolysis, a protein with a low molecular weight, by an enzyme called kallikrein.

Kallikreins (KLK) are a group of serine proteases that are found in different biological tissues and fluids. Kallikreins are divided into two principal categories: plasma kallikreins and tissue kallikreins [Paliouras et al., "*The kallikrein world: an update on the human tissue Kallikreins*", Biol. Chem., (2006), 387, 643-652]. Both categories differ significantly in their molecular weight, substrate specificity, immunological characteristics and genetic structure.

Tissue kallikreins are extracellular serine proteases secreted by granular keratinocytes [Eissa et al., "Human tissue kallikreins as promiscuous modulators of homeostatic skin barrier functions". Biol. Chem., (2008), 389, 669-680].

The principal kallikreins in the stratum corneum are the KLK5, the KLK7 and the KLK14, although multiple KLKs have been detected by immunohistochemistry in the granular stratum and in the stratum corneum, both in their active and inactive form. It has been found that they are responsible for the activation of antimicrobial peptides after an infection, as well as degrading molecules responsible for adhesion between corneocytes. Kallikrein mRNA has also been detected in the epithelium follicles, which suggests the participation of KLKs in the development of hair. Furthermore, they also participate in the activity of the sebaceous glands and the formation of sebum.

KLKs are activated by means of a series of reactions in which a KLK activates a pro-KLK, thus a KLK acts as an initiator, propagator and/or executor, depending on its concentration, specificity and activity level, as with a free-radical reaction. In in vitro studies, it has been demonstrated that pro-KLK5 is activated by KLK14 and that KLK5 activates pro-KLK7 and pro-KLK14.

It has been found that in skin affected by rosacea there are levels of KLK5 higher than in healthy skin [Yamasaki et al., "Kallikrein-mediated proteolysis regulates the antimicrobial effects of cathelicidins in skin", the FASEB J., (2006), 20, 2068-2080]. It has also been observed that in skin affected by rosacea there is a high level of cathelicidin, a antimicrobial peptide that is processed by the enzymes of the stratum corneum such as kallikreins giving rise to its active form LL-37 involved in the inflammation and in angiogenesis [Morizane et al., "TLR2 Expression Is Increased in Rosacea and Stimulates Enhanced Serine Protease Production by Keratinocytes" J Invest Dermatol., (2010), 130(5), 1297-1306] inducing cytokine release such as interleukins (IL-6, IL-8, etc.), which are known inflammatory agents [Pistolic J et al, Host defense peptide LL-37 induces IL-6 expression in human bronchial epithelial cells by activation of the NF-kappaB signaling pathway, J Innate Immun. 2009; 1(3): 254-67].

Another of the more common vascular disorders of the skin is the appearance of telangiectasias, which are generally presented as superficial cutaneous capillaries near the surface of the skin with part of the center being bright red and with radial branches. This skin condition is also known as spider veins. Telangiectasia can be stimulated by the exposure to UV radiation, stress, environmental factors, lesions and/or the aging of the skin.

Appearance of Wrinkles and Loss of Firmness

Collagen is the most abundant protein in the skin, comprising between 70-80% of the dry weight of the skin, and gives it the mechanical and structural integrity necessary to maintain its functions. There are numerous types of collagen, collagen I being the most common. It is structured in the form of fibrils that are also associated by forming collagen fibers in a process called fibrillogenesis. Other types of collagen are III, IV, VII and XII. The second most important protein in the dermis is elastin. Elastin is organized in the form of insoluble elastic fibers with a central hydrophobic nucleus surrounded by fibrillar structures. It is more of a minority protein than collagen, but is crucial in the maintenance of the elasticity and resistance of the skin.

This extra cellular connective tissue of the dermis can be damaged as a result of an inflammatory response. Aggressive climates or exposure to UV light stimulate the production of reactive species which boost the inflammatory processes of the skin and activate the proteolytic systems of the extra cellular matrix. Phagocytes released into the skin through the blood vessels can also release proteases that cause inflammation and activate matrix metalloproteinases (MMP). These MMPs degrade the collagen and elastin molecules which may have been damaged after the inflammatory process. MMP-1 degrades collagen I and III, whilst MMP-12 is the most active against elastin. The result of excessive collagen and elastin degradation is flaccid and wrinkled skin.

During aging cytokines are released (the inflammaging theory), which as well as causing inflammation, are metalloprotease (MMP) activators such as collagenase, responsible for the degradation of the principle proteins that form the extra cellular matrix of the dermis and are responsible for physically supporting the whole structure of the skin such as collagen and elastin. Cytokines are also released through exposure to ultraviolet light, one of the major causes of inflammation and photoaging of the skin.

The release of cytokines that takes place in different conditions, disorders or diseases of the skin that have an inflammatory component also affects the quality of the skin. For example, those affected by rosacea present high levels of LL-37, which in turn inhibits the expression of collagen I and III [Park H. J et al., "*Collagen synthesis is suppressed in dermal fibroblasts by the human antimicrobial peptide LL-37*", *J Invest Dermatol,* 2009, 129, 843-850], which, together with a greater activity of MMPs later in life makes skin with rosacea much weaker and flaccid.

Pigmentation of the Skin

The color of the skin is chiefly determined by the quantity, distribution and type of melanin, a natural pigmented biopolymer that is synthesized in melanosomes, organules present in the melanocytes of the epidermis, in a process called melanogenesis catalyzed by tyrosinase. Tyrosinase catalyzes the two first decisive steps of melanogenesis: hydroxylation of tyrosine to form 3,4-hydroxyphenylalanine (DOPA) and the subsequent oxidation of DOPA to form DOPA-quinone. Subsequently, melanin synthesized in the melanocytes is transferred through dendrites to the keratinocytes, from where it will be distributed through the whole epidermis and the stratum corneum. This is the process that determines the coloring of the skin.

Modification of the natural pigmentation of the skin is desirable for different reasons for many people in America, Asia or Europe. Among the reasons for modifying the natural color of the skin is the search for clearer skin by beauty models and the removal or reduction of marks on the skin such as freckles or lentigines.

People affected by skin disorders or diseases with an inflammatory component are exposed to developing postinflammatory hyperpigmentation. The coloring of the skin has been a motive for concern for human beings for many years. In particular, the ability to remove hyperpigmentation, whether it is due to age (marks, freckles or general aging of the skin), or whether it is due to disorders or diseases (melasma, chloasma, post-inflammatory hyperpigmentation) is of interest for individuals who want a uniform skin tone. Furthermore, when exposure to UV radiation is prolonged or excessive, cancerous hyperpigmented lesions or melanomas can develop [Dooley T. P., "*Recent advances in cutaneous melanoma oncogenesis research*", (1994), *Onco. Res.,* 6, 1-9] as well as benign hyperpigmented marks due to photoaging and excessive functioning of melanocytes, which synthesize more melanin than is required in an attempt to regenerate damaged skin after the inflammatory process. The result of an increase in synthesis and release of mediatory substances of inflammation such as cytokines, TNF-α, interleukin-6 and interleukin-8 is hyperpigmented skin.

The cosmetic industry has undertaken considerable efforts to develop new compounds useful in the treatment and/or care of conditions, disorders and/or diseases that improve or are prevented by the inhibition of cytokine release, the inhibition of matrix metalloproteinase activity and/or the inhibition of melanogenesis. However, although the majority of the existing compounds in the prior art are useful for the treatment and/or care of conditions, disorders and/or diseases that improve or are prevented by one or several of the aforementioned activities, it is difficult to find in the prior art compounds that present all of the aforementioned activities at the same time.

DETAILED DESCRIPTION OF THE INVENTION

This invention provides an alternative to the aforementioned problem. Surprisingly, the applicant of this invention has found that certain synthetic compounds have significant effectiveness in the treatment and/or care of the skin and/or mucous membranes, and in particular they are useful for the treatment and/or care of those conditions, disorders and/or diseases that improve or are prevented, delayed, or hindered by the inhibition of cytokine release, the inhibition of matrix metalloproteinases activity of and/or the inhibition of melanogenesis.

Definitions

In order to facilitate the comprehension of this invention, the meanings of some terms and expressions as used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others.

In the context of this invention "care of the skin" comprises the delay or hindering of the signs of aging and/or photoaging.

The term "treatment", according to its use in the context of this document when not accompanied by the qualifications "cosmetic, non-therapeutic", means the administration of a compound according to the invention to alleviate or eliminate a disease or disorder or reduce or eliminate one or more symptoms associated with said disease or disorder. The term "treatment" also covers alleviate or eliminating the physiological consequences of the disease or disorder.

When the term "treatment" is accompanied by the qualifications "cosmetic, non-therapeutic" they refer to the application of the compound to the skin and/or mucous membranes in particular in order to improve the cosmetic qualities of the skin and/or mucous membranes, for example and not restricted to, their degree of hydration, elasticity, firmness, shine, tone or texture, among others. The term "care" refers in this invention to the maintenance of the qualities of the skin and/or mucous membranes. Said qualities are able to be improved or maintained by means of a cosmetic treatment and/or care of the skin and/or mucous membranes both in healthy subjects and those that present diseases and/or disorders of the skin and/or mucous membranes, for example and not restricted to, ulcers and injuries on the skin, psoriasis, dermatitis, acne and rosacea, among others.

The term "prevention", as used in this invention, refers to the ability of a compound of the invention to prevent the appearance or the development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, for example and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of several environmental factors such as exposure to tobacco smoke, exposure to pollution, and climatic conditions such as cold and/or wind also contribute to the aging of the skin.

In this description the abbreviations used for amino acids follows the rules of IUPAC-IUB Commission of Biochemical Nomenclature specified in *Eur. J. Biochem.* (1984) 138:9-37.

Thus, for example, Val represents $NH_2$—$CH(CH(CH_3)_2)$—COOH, Val- represents $NH_2$—$CH(CH(CH_3)_2)$—CO—, -Val represents —NH—$CH(CH(CH_3)_2)$—COOH and -Val- represents —NH—$CH(CH(CH_3)_2)$—CO—. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acids residues and their nomenclature in one and three-letter code

| Name | Residue | Symbol | Residue |
|------|---------|--------|---------|
| Asparagyl -Asn- N | (structure) | Arginyl -Arg- R | (structure) |
| Valyl -Val- V | (structure) | Alanyl -Ala- A | (structure) |
| Theonyl -Thr- T | (structure) | Seryl -Ser- S | (structure) |

The abbreviation "Ac—" is used in this description to designate the acetyl group ($CH_3$—CO—), the abbreviation "Palm-" is used to designate the palmitoyl group ($CH_3$—$(CH_2)_{14}$—CO—).

The term "non-cyclic aliphatic group" is used in this invention to cover, for example and not restricted to, the linear or branched alkyl, alkenyl and alkynyl groups.

The term "alkyl group" refers to a linear or branched saturated group, which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a simple bond, including, for example and not restricted to, the vinyl, oleyl, linoleyl and similar groups.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a simple bond, including, for example and not restricted to, the ethynyl group, 1-propinyl, 2-propinyl, 1-butinyl, 2-butinyl, 3-butinyl, pentinyl, such as 1-pentinyl, and similar. The alkynyl groups can also contain one or more double carbon-carbon bonds, including, for example and not restricted to, the but-1-en-3-inyl, pent-4-en-1-inyl groups and similar.

The term "alycyclyl group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a simple bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, which is bound to the rest of the molecule by a simple bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, which is bound to the rest of the molecule by a simple bond, including, for example and not restricted to, the cycloct-2-in-1-yl group and similar. Cycloalkynyl groups can also contain one or more double carbon-carbon bonds, including, for example and not restricted to, the cycloct-4-en-2-inyl group and similar.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl, among others; or to an aralkyl group.

The term "aralkyl group" refers to an alkyl group substituted by an aromatic group, with between 7 and 24 carbon atoms and including, for example and not restricted to, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$—CH(phenyl)$_2$ and similar.

The term "heterocyclyl group" refers to a hydrocarbonated ring of 3-10 members, in which one or more of the atoms in the ring, preferably 1, 2 or 3 of the atoms in the ring, is a different element to carbon, such as nitrogen, oxygen or sulfur and it can be saturated or unsaturated. For the purposes of this invention, the heterocycle can be a cyclic, monocyclic, bicyclic or tricyclic system, which may include systems of fused rings; and the nitrogen, carbon or sulfur atoms in the heterocyclyl radical may be optionally oxidized; the nitrogen atom may be optionally quaternized; and the heterocyclyl radical may be partially or completely saturated or be aromatic. The greatest preference is for the term heterocyclyl to refer to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups are pyridine, pyrrol, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms different to carbon including, for example and not restricted to, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and similar.

As it is understood in this technical field, there may be a certain degree of substitution of the aforementioned groups. Therefore, there can be substitution in any of the groups of this invention. The references in this document to substituted groups in the groups of this invention indicate that the specified radical can be substituted in one or more positions available by one or more substitutes, preferably in 1, 2 or 3 positions, more preferably in 1 or 2 positions, yet more preferably in 1 position. These substituents include, for example and not restricted to, alkyl C$_1$-C$_4$; hydroxyl; alcoxyl C$_1$-C$_4$; amino; aminoalkyl C$_1$-C$_4$; carbonyloxyl C$_1$-C$_4$; oxycarbonyl C$_1$-C$_4$; halogen such as fluoride, chlorine, bromine and iodine; cyano; nitro; azide; alkylsulfonyl C$_1$-C$_4$; thiol; alkylthio C$_1$-C$_4$; aryloxy such as phenoxyl; —NR$_b$(C=NR$_b$)NR$_b$R$_c$; wherein R$_b$ and R$_c$ are independently selected from the group formed by H, alkyl C$_1$-C$_4$, alkenyl C$_2$-C$_4$, alkynyl C$_2$-C$_4$, cycloalkyl C$_3$-C$_{10}$, aryl C$_6$-C$_{18}$, aralkyl C$_7$-C$_{17}$, heterocyclyl of 3-10 members or protective group of the amino group.

Compounds in the Invention

A first aspect of the invention refers to a compound of general formula (I),

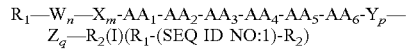

R$_1$—W$_n$—X$_m$-AA$_1$-AA$_2$-AA$_3$-AA$_4$-AA$_5$-AA$_6$-Y$_p$—Z$_q$—R$_2$(I)(R$_1$-(SEQ ID NO:1)-R$_2$)

its stereoisomers, mixtures thereof and/or its cosmetically or pharmaceutically acceptable salts, where AA$_1$ is selected from the group formed by -Ser- and a bond;

AA$_2$ is selected from the group formed by -Val- and -Ala-;

AA$_3$ is selected from the group formed by -Arg- and -Thr-;

AA$_4$ is selected from the group formed by -Val- and -Asn-;

AA$_5$ is selected from the group formed by -Ala- and -Thr-;

AA$_6$ is selected from the group formed by -Val- and a bond;

W, X, Y, Z are amino acids and are independently selected from amongst themselves;

n, m, p and q are independently selected from amongst themselves and have a value of 0 or 1;

n+m+p+q is smaller or equal to 2;

with the condition that if $AA_1$ is a bond, $AA_2$ is -Ala-, $AA_4$ is -Val- and $AA_6$ is a bond, then $AA_5$ is -Thr-;

with the condition that if $AA_1$ is a bond, $AA_2$ is -Val-, $AA_3$ is -Thr-, $AA_4$ is -Val- and $AA_6$ is a bond, then $AA_5$ is -Ala-;

with the condition that if $AA_1$ is a bond, $AA_2$ is -Val-, $AA_3$ is -Thr-, $AA_4$ is -Asn-, and $AA_6$ is -Val-, then $AA_5$ is -Ala-;

with the condition that if $AA_1$ is a bond, $AA_2$ is -Val-, $AA_3$ is -Arg-, $AA_4$ is -Val-, and $AA_6$ is -Val-, then $AA_5$ is -Thr-;

with the condition that if $AA_1$ is a bond, $AA_2$ is -Val-, $AA_3$ is -Thr-, $AA_4$ is -Asn-, $AA_5$ is -Ala- and $AA_6$ is a bond, then n+m+p+q is equal to 0;

with the condition that if $AA_1$ is a bond, $AA_2$ is -Ala-, $AA_3$ is -Thr-, $AA_4$ is -Val-, $AA_6$ is a bond and p+q is greater or equal to 1, then $AA_5$ is -Ala-;

with the condition that if $AA_1$ is a bond, $AA_2$ is -Ala-, $AA_3$ is -Thr-, $AA_4$ is -Asn-, $AA_5$ is -Thr- and $AA_6$ is a bond, then n+m+p+q is smaller or equal to 1;

with the condition that if $AA_1$ is a bond, $AA_2$ is -Ala-, $AA_3$ is -Thr-, $AA_4$ is -Asn-, $AA_6$ is a bond, X is -Gly- and W is -Leu-, then $AA_5$ is -Thr-;

with the condition that if $AA_1$ is a bond, $AA_2$ is -Val-, $AA_3$ is -Thr-, $AA_4$ is -Val-, $AA_5$ is -Ala-, $AA_6$ is a bond, then p and q are 0;

with the condition that if $AA_1$ is a bond, $AA_2$ is -Ala-, $AA_3$ is -Arg-, $AA_4$ is -Val-, $AA_6$ is a bond, Y is Ala, and Z is -Leu-, then $AA_5$ is -Ala-;

$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ or $R_2$ are not α-amino acids.

Groups $R_1$ and $R_2$ are bound to the amino-terminal ends (N-terminal) and carboxy-terminal (C-terminal) of the peptide sequences respectively.

In accordance with a preferred embodiment $R_1$ is selected from the group formed by H, a polymer derived from polyethylene glycol and $R_5$—CO—, wherein $R_5$ is selected from the group formed by substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms and $R_5$—CO— is not an α-amino acid. More preferably, $R_1$ is selected from the group formed by H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is selected from the group formed by —$NR_3R_4$, —$OR_3$, —$SR_3$, wherein $R_3$ and $R_4$ are independently selected from the group formed by H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_3R_4$ is not an α-amino acid. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$. More preferably, $R_3$ and $R_4$ are independently selected from the group formed by H, a polymer derived from polyethylene glycol with a molecular weight comprised between 200 and 35000 Daltons, methyl, ethyl, hexyl, dodecyl and hexadecyl. Even more preferably $R_3$ is H and $R_4$ is selected from the group formed by H, methyl, ethyl, hexyl, dodecyl and hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl and palmitoyl, preferably $R_1$ is selected from the group formed by H, acetyl and palmitoyl and $R_2$ is selected from the group formed by —OH and —$NH_2$.

In accordance with another particular embodiment the most preferred structures of the polymer derived from polyethylene glycol are the group (—$CH_2$—$CH_2$—O)$_r$—H in which r is a number comprised between 4 and 795 and the group

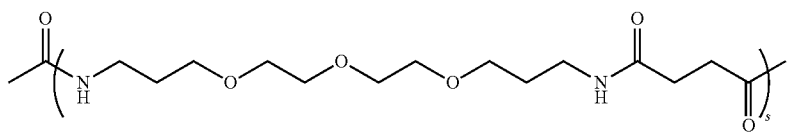

where s is a number between 1 and 125.

In accordance with another embodiment of this invention n, m, p and q are 0.

In accordance with another embodiment of this invention $R_1$ is selected from the group formed by H, acetyl, lauroyl, myristoyl and palmitoyl, $AA_1$ is -L-Ser, $AA_2$ is -L-Val-, AA$_3$ is -L-Arg-, AA$_4$ is -L-Val-, AA$_5$ is -L-Ala-, AA$_6$ is -L-Val- and R$_2$ is selected from the group formed by —NR$_3$R$_4$ and —OR$_3$ wherein R$_3$ and R$_4$ are independently selected from H, methyl, ethyl, hexyl, dodecyl and hexadecyl, preferably R$_2$ is —OH or —NH$_2$. More preferably, R$_1$ is acetyl or palmitoyl and R$_2$ is —NH$_2$. Even more preferably, n, m, p and q are 0.

In accordance with another embodiment of this invention R$_1$ is selected from the group formed by H, acetyl, lauroyl, myristoyl and palmitoyl, AA$_1$ is a bond, AA$_2$ is -L-Ala-, AA$_3$ is -L-Thr-, AA$_4$ is -L-Asn-, AA$_5$ is -L-Thr-, AA$_6$ is a bond and R$_2$ is selected from the group formed by —NR$_3$R$_4$ and —OR$_3$ wherein R$_3$ and R$_4$ are independently selected from H, methyl, ethyl, hexyl, dodecyl and hexadecyl, preferably R$_2$ is —OH or —NH$_2$. More preferably, R$_1$ is acetyl or palmitoyl and R$_2$ is —NH$_2$. Even more preferably, n, m, p and q are 0.

Specifically, the compounds of the invention, represented according to the formula (I) are selected from the group of peptide sequences outlined in Table 2:

TABLE 2

Ac-Ser-Val-Arg-Val-Ala-Val-NH$_2$ (Ac-(SEQ ID NO: 2)-NH$_2$)

Ac-Ser-Ala-Arg-Val-Ala-Val-NH$_2$ (Ac-(SEQ ID NO: 3)-NH$_2$)

Ac-Ser-Val-Thr-Val-Ala-Val-NH$_2$ (Ac-(SEQ ID NO: 4)-NH$_2$)

Ac-Ser-Val-Arg-Asn-Ala-Val-NH$_2$ (Ac-(SEQ ID NO: 5)-NH$_2$)

Ac-Ser-Val-Arg-Val-Thr-Val-NH$_2$ (Ac-(SEQ ID NO: 6)-NH$_2$)

Ac-Ser-Ala-Thr-Val-Ala-Val-NH$_2$ (Ac-(SEQ ID NO: 7)-NH$_2$)

Ac-Ser-Ala-Arg-Asn-Ala-Val-NH$_2$ (Ac-(SEQ ID NO: 8)-NH$_2$)

Ac-Ser-Ala-Arg-Val-Thr-Val-NH$_2$ (Ac-(SEQ ID NO: 9)-NH$_2$)

Ac-Ser-Val-Thr-Asn-Ala-Val-NH$_2$ (Ac-(SEQ ID NO: 10)-NH$_2$)

Ac-Ala-Arg-Asn-Thr-NH$_2$ (Ac-(SEQ ID NO: 11)-NH$_2$)

Ac-Ala-Thr-Val-Thr-NH$_2$ (Ac-(SEQ ID NO: 12)-NH$_2$)

Ac-Ala-Thr-Asn-Ala-NH$_2$ (Ac-(SEQ ID NO: 13)-NH$_2$)

Ac-Val-Thr-Asn-Thr-NH$_2$ (Ac-(SEQ ID NO: 14)-NH$_2$)

Ac-Ala-Arg-Asn-Ala-NH$_2$ (Ac-(SEQ ID NO: 15)-NH$_2$)

Ac-Ala-Thr-Asn-Thr-NH$_2$ (Ac-(SEQ ID NO: 16)-NH$_2$)

Ac-Ser-Ala-Arg-Val-Ala-Val-NH-(CH$_2$)$_{15}$-CH$_3$ (Ac-(SEQ ID NO: 3)-NH-(CH$_2$)$_{15}$-CH$_3$)

Ac-Ser-Val-Arg-Asn-Ala-Val-NH-(CH$_2$)$_{15}$-CH$_3$ (Ac-(SEQ ID NO: 5)-NH-(CH$_2$)$_{15}$-CH$_3$)

Ac-Ser-Val-Arg-Val-Thr-Val-NH-(CH$_2$)$_{15}$-CH$_3$ (Ac-(SEQ ID NO: 6)-NH-(CH$_2$)$_{15}$-CH$_3$)

Ac-Ser-Val-Arg-Val-Ala-Val-NH-(CH$_2$)$_{15}$-CH$_3$ (Ac-(SEQ ID NO: 2)-NH-(CH$_2$)$_{15}$-CH$_3$)

Ac-Ala-Thr-Asn-Ala-NH-(CH$_2$)$_{15}$-CH$_3$ (Ac-(SEQ ID NO: 13)-NH-(CH$_2$)$_{15}$-CH$_3$)

Ac-Ala-Arg-Asn-Thr-NH-(CH$_2$)$_{15}$-CH$_3$ (Ac-(SEQ ID NO: 11)-NH-(CH$_2$)$_{15}$-CH$_3$)

Ac-Val-Thr-Asn-Thr-NH-(CH$_2$)$_{15}$-CH$_3$ (Ac-(SEQ ID NO: 14)-NH-(CH$_2$)$_{15}$-CH$_3$)

Ac-Ala-Thr-Asn-Thr-NH(CH$_2$)$_{15}$CH$_3$ (Ac-(SEQ ID NO: 16)-NH-(CH$_2$)$_{15}$-CH$_3$)

Palm-Ser-Val-Thr-Val-Ala-Val-Ala-Leu-NH$_2$ (Palm-(SEQ ID NO: 17)-NH$_2$)

Palm-Ile-Ile-Ser-Ala-Arg-Val-Ala-Val-NH$_2$ (Palm-(SEQ ID NO: 18)-NH$_2$)

Palm-Ser-Ala-Arg-Val-Ala-Val-Ala-NH$_2$ (Palm-(SEQ ID NO: 19)-NH$_2$)

Palm-Leu-Ser-Val-Thr-Val-Ala-Val-NH$_2$ (Palm-(SEQ ID NO: 20)-NH$_2$)

Palm-Ser-Val-Arg-Val-Ala-Val-NH$_2$ (Palm-(SEQ ID NO: 2)-NH$_2$)

Palm-Ser-Val-Arg-Asn-Ala-Val-NH$_2$ (Palm-(SEQ ID NO: 5)-NH$_2$)

Palm-Ser-Ala-Arg-Val-Ala-Val-NH$_2$ (Palm-(SEQ ID NO: 3)-NH$_2$)

Palm-Ser-Val-Arg-Val-Thr-Val-NH$_2$ (Palm-(SEQ ID NO: 6)-NH$_2$)

Palm-Ser-Val-Thr-Val-Ala-Val-NH$_2$ (Palm-(SEQ ID NO: 4)-NH$_2$)

Palm-Gly-Ala-Ala-Thr-Asn-Ala-NH$_2$ (Palm-(SEQ ID NO: 21)-NH$_2$)

Palm-Val-Thr-Asn-Thr-NH$_2$ (Palm-(SEQ ID NO: 14)-NH$_2$)

TABLE 2-continued

Palm-Ala-Thr-Val-Thr-NH$_2$ (Palm-(SEQ ID NO: 12)-NH$_2$)

Palm-Ala-Thr-Asn-Ala-NH$_2$ (Palm-(SEQ ID NO: 13)-NH$_2$)

Palm-Ala-Thr-Asn-Thr-NH$_2$ (Palm-(SEQ ID NO: 16)-NH$_2$)

Palm-Ala-Arg-Asn-Thr-NH$_2$ (Palm-(SEQ ID NO: 11)-NH$_2$)

H-Ser-Val-Arg-Val-Ala-Val-NH$_2$ (H-(SEQ ID NO: 2)-NH$_2$)

H-Ser-Val-Arg-Val-Ala-Val-OH (H-(SEQ ID NO: 2)-OH)

H-Ala-Thr-Asn-Thr-OH (H-(SEQ ID NO: 16)-OH)

Ac-Gly-Val-Ala-Arg-Asn-Thr-OH (Ac-(SEQ ID NO: 22)-OH)

Ac-Ser-Val-Arg-Asn-Ala-Val-OH (Ac-(SEQ ID NO: 5)-OH)

Ac-Ser-Ala-Arg-Val-Ala-Val-OH (Ac-(SEQ ID NO: 3)-OH)

Ac-Ser-Val-Thr-Val-Ala-Val-OH (Ac-(SEQ ID NO: 4)-OH)

Ac-Ser-Val-Arg-Val-Ala-Val-OH (Ac-(SEQ ID NO: 2)-OH)

Ac-Ser-Ala-Thr-Val-Ala-Val-OH (Ac-(SEQ ID NO: 7)-OH)

Ac-Ser-Ala-Thr-Asn-Thr-Val-OH (Ac-(SEQ ID NO: 23)-OH)

Ac-Val-Ser-Val-Arg-Val-Ala-Val-OH (Ac-(SEQ ID NO: 24)-OH)

Ac-Ser-Ala-Thr-Asn-Thr-Val-Ala-OH (Ac-(SEQ ID NO: 25)-OH)

Ac-Val-Ser-Val-Arg-Val-Ala-Val-Ala-OH (Ac-(SEQ ID NO: 26)-OH)

Ac-Ser-Ala-Thr-Asn-Thr-OH (Ac-(SEQ ID NO: 27)-OH)

Ac-Ser-Val-Arg-Val-Ala-OH (Ac-(SEQ ID NO: 28)-OH)

Ac-Ala-Arg-Asn-Thr-OH (Ac-(SEQ ID NO: 11)-OH)

Ac-Ala-Thr-Asn-Ala-OH (Ac-(SEQ ID NO: 13)-OH)

Ac-Val-Arg-Asn-Thr-OH (Ac-(SEQ ID NO: 29)-OH)

Ac-Ala-Thr-Asn-Thr-OH (Ac-(SEQ ID NO: 16)-OH)

Ac-Ala-Thr-Val-Thr-OH (Ac-(SEQ ID NO: 12)-OH)

Ac-Val-Thr-Asn-Ala-OH (Ac-(SEQ ID NO: 30)-OH)

Palm-Ser-Ala-Arg-Val-Ala-Val-Arg-Lys-OH (Palm-(SEQ ID NO: 31)-OH)

Palm-Ser-Val-Arg-Val-Ala-Val-OH (Palm-(SEQ ID NO: 32)-OH)

Palm-Val-Thr-Asn-Thr-Gln-Phe-OH (Palm-(SEQ ID NO: 33)-OH)

Palm-Ser-Val-Thr-Val-Ala-Val-OH (Palm-(SEQ ID NO: 4)-OH)

Palm-Ser-Ala-Arg-Val-Thr-Val-OH (Palm-(SEQ ID NO: 9)-OH)

Palm-Ser-Val-Arg-Asn-Ala-Val-OH (Palm-(SEQ ID NO: 5)-OH)

Palm-Ser-Ala-Arg-Val-Ala-Val-OH (Palm-(SEQ ID NO: 3)-OH)

Palm-Ala-Thr-Asn-Ala-Val-OH (Palm-(SEQ ID NO: 34)-OH)

Palm-Ala-Arg-Asn-Ala-OH (Palm-(SEQ ID NO: 15)-OH)

Palm-Val-Thr-Asn-Thr-OH (Palm-(SEQ ID NO: 14)-OH)

Palm-Ala-Thr-Val-Thr-OH (Palm-(SEQ ID NO: 12)-OH)

Palm-Ala-Thr-Asn-Thr-OH (Palm-(SEQ ID NO: 16)-OH)

Ac-Ser-Val-Arg-Asn-Ala-Val-Val-Leu-NH$_2$ (Ac-(SEQ ID NO: 35)-NH$_2$)

Ac-Val-Ser-Val-Arg-Val-Ala-Val-Ala-NH$_2$ (Ac-(SEQ ID NO: 26)-NH$_2$)

Ac-Ser-Ala-Thr-Asn-Thr-Val-Ala-NH$_2$ (Ac-(SEQ ID NO: 25)-NH$_2$)

TABLE 2-continued

```
Ac-Ile-Ser-Val-Thr-Val-Ala-Val-NH₂ (Ac-(SEQ ID NO: 36)-NH₂)

Ac-Ser-Ala-Arg-Asn-Thr-NH₂ (Ac-(SEQ ID NO: 37)-NH₂)

Ac-Ser-Ala-Thr-Val-Thr-NH₂ (Ac-(SEQ ID NO: 38)-NH₂)

Ac-Ser-Ala-Thr-Asn-Ala-NH₂ (Ac-(SEQ ID NO: 39)-NH₂)

Ac-Ala-Arg-Asn-Thr-Val-NH₂ (Ac-(SEQ ID NO: 40)-NH₂)

Ac-Ala-Thr-Val-Thr-Val-NH₂ (Ac-(SEQ ID NO: 41)-NH₂)

Ac-Ala-Thr-Asn-Ala-Val-NH₂ (Ac-(SEQ ID NO: 42)-NH₂)

H-Ala-Thr-Asn-Thr-NH(CH₂)₁₅CH₃ (H-(SEQ ID NO: 16)-NH(CH₂)₁₅CH₃)

H-Ser-Val-Arg-Val-Ala-Val-NH(CH₂)₁₅CH₃ (H-(SEQ ID NO: 32)-NH(CH₂)₁₅CH₃
```

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that $AA_1$ can be Ser, it is understood that $AA_1$ is selected from -L-Ser-, -D-Ser- or mixtures of both, racemic or non-racemic. In the same way, when it is said that $AA_2$ can be -Ala-, it is understood that it can be -L-Ala-, -D-Ala- or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoyc acid, 1-naphthylalanine, 2-naphthylalanine, 2-aminobenzoic acid, 4-aminobenzoic acid, 4-chlorophenylalanine, 2,3-diaminopropionic acid, 2,4 diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "Unusual amino acids in peptide synthesis" by D. C. Roberts and F. Vellaccio, in *The Peptides, Vol. 5* (1983), Chapter VI, Gross E. and Meienhofer J., Eds., Academic Press, New York, USA or in the commercial catalogues of the companies specialized in the field.

In the context of this invention, when n, m, p or q are not 0 it is clearly understood that the nature of W, X, Y and/or Z does not hinder the activity of the compounds of the invention, but it contributes to the inhibition of cytokine release, the inhibition of matrix metalloproteinases activity and/or the inhibition of melanogenesis or has no effect on it.

The cosmetically and pharmaceutically acceptable salts of the compounds provided by this invention are also found within the field of this invention. The term "cosmetically or pharmaceutically acceptable salts" means a salt recognized for its use in animals and more specifically in human beings, and includes salts used to form base addition salts, either they are inorganic, for example and not restricted to, lithium, sodium, potassium, calcium, magnesium, manganese, copper, zinc or aluminum, among others, or they are organic, for example and not restricted to, ethylamine, diethylamine, ethylenediamine, ethanolamine, diethanolamine, arginine, lysine, histidine or piperazine among others, or acid addition salts, either they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the compounds of the invention can be obtained by the conventional methods, well known in the prior art [Berge S. M. et al., "*Pharmaceutical Salts*", (1977), *J. Pharm. Sci.*, 66, 1-19].

Preparation Procedures of the Compounds of the Invention

Synthesis of the peptides of the invention, their stereoisomers, mixtures thereof and/or their cosmetically or pharmaceutically acceptable salts can be carried out according to conventional methods, known in the prior art, such as using solid phase peptide synthesis methods [Stewart J. M. and Young J. D., "*Solid Phase Peptide Synthesis, 2nd edition*", (1984), Pierce Chemical Company, Rockford, Ill.; Bodanzsky M. and Bodanzsky A., "*The practice of Peptide Synthesis*", (1994), Springer Verlag, Berlin; Lloyd-Williams P. et al., "*Chemical Approaches to the Synthesis of Peptides and Proteins*", (1997), CRC, Boca Raton, Fla., USA], synthesis in solution, a combination of the methods of solid phase synthesis and in solution or enzymatic synthesis [Kullmann W. "*Proteases as catalysts for enzymic syntheses of opioid peptides*", (1980), *J. Biol. Chem.*, 255(17), 8234-8238]. The compounds can also be obtained by fermentation of a bacterial strain, modified or unmodified, by genetic engineering to produce the desired sequences, or by controlled hydrolysis of proteins with animal or plant origin, preferably plant, which free peptide fragments that contain, at least, the desired sequence.

For example, a method of obtaining the compounds (I) of the invention, their stereoisomers and mixtures thereof comprises the stages of:

coupling of an amino acid, with the N-terminal end protected and the C-terminal end free, with an amino acid with the N-terminal end free and the C-terminal end protected or bound to a solid support;

elimination of the protective group of the N-terminal end;

repetition of the coupling sequence and elimination of the protective group of the N-terminal end until the desired peptide sequence is obtained;

elimination of the protective group of the C-terminal end or cleavage of the solid support.

Preferably, the C-terminal end is bound to a solid support and the process is carried out in solid phase and, therefore, comprises the coupling of an amino acid with the N-terminal end protected and the C-terminal end free with an amino acid with the N-terminal end free and the C-terminal end bound to a polymeric support; elimination of the protective group of the N-terminal end; and repetition of this sequence as many times as is necessary to thus obtain the compound of the desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or an amino acid previously bound to the polymeric support. Convergent synthesis strategies are widely known by persons skilled in the art and are described in Lloyd-Williams P. et al., "*Convergent Solid-Phase Peptide Synthesis*", (1993), *Tetrahedron,* 49(48), 11065-11133.

The process can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound, wherein $R_1$ has the aforementioned meaning and X is a leaving group, for example and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric support.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl) ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-1-(4,4-dimethyl-2,6-dioxocyclohex-1-ylidene)ethyl (Dde), 1-(4,4-dimethyl-2,6-dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt tester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The threonine and serine side chain can be protected with a protective group selected from the group formed by tBu, Bzl, Trt and Ac. The amide group of the asparagine side chain can be protected by the Trt group or the xanthyl group (Xan) or can be used unprotected. The arginine side chain is protected with a protective group selected from the group formed by Tos, 4-methoxy-2,3,6-trimethylbenzenesulfonyl (Mtr), Alloc, nitro, 2,2,4,6,7-pentamethyldihydrobenzofuran-5-sulfonyl (Pbf) and 2,2,5,7,8-pentamethylchroman-6-sulfonyl (Pmc).

In a preferred embodiment, the protective group strategy used is the strategy wherein the amino groups are protected by Boc, the carboxyl groups are protected by Bzl, cHx or All esters, the threonine and serine side chain is protected with the Bzl group, the arginine side chain is protected with Tos, and asparagine is used unprotected in its side chain.

In another preferred embodiment, the protective group strategy used is the strategy wherein the amino groups are protected by Fmoc, the carboxyl groups are protected by tBu, All or Trt esters, the threonine and serine side chain is protected with tBu, the arginine side chain is protected with the Pmc or Pbf group, asparagine is used protected with the Trt group in its side chain.

Examples of these and additional protective groups, their introduction and elimination, can be found in the literature

[Atherton B. and Sheppard R. C., "*Solid Phase Peptide Synthesis: A practical approach*", (1989), IRL Oxford University Press]. The term "protective groups" also includes the polymeric supports used in solid phase synthesis.

When synthesis takes place totally or partially in solid phase, the possible solid supports used in the process of the invention involve polystyrene support, polyethylene glycol grafted to polystyrene and similar, for example and not restricted to, p-methylbenzhydrylamine resins (MBNA) [Matsueda G. R. et al., "*A p-methylbenzhydrylamine resin for improved solid-phase synthesis of peptide amides*", (1981), *Peptides*, 2, 45-50], 2-chlorotrityl resins [Barlos K. et al., "*Darstellung geschützter Peptid-Fragmente unter Einsatz substituierter Triphenylmethyl-Harze*", (1989), *Tetrahedron Lett.*, 30, 3943-3946; Barlos K. et al., "*Veresterung von partiell geschützten Peptid-Fragmenten mit Harzen. Einsatz von 2-Chlortritylchlorid zur Synthese von Leu1-Gastrin I*", (1989), *Tetrahedron Lett.*, 30, 3947-3951], TentaGel resins (Rapp Polymere GmbH), ChemMatrix resins (Matrix Innovation, Inc.) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions*", (1990), *J. Org. Chem.*, 55, 3730-3743], 2-[4-aminomethyl-(2,4-dimethoxyphenyl)] phenoxyacetic acid (AM) [Rink H., "*Solid-phase synthesis of protected peptide fragments using a trialkoxy-diphenyl-methylester resin*", (1987), *Tetrahedron Lett.*, 28, 3787-3790], Wang [Wang S. S., "*p-Alkoxybenzyl Alcohol Resin and p-Alkoxybenzyloxycarbonylhydrazide Resin for Solid Phase Synthesis of Protected Peptide Fragments*"; (1973), *J. Am. Chem. Soc.*, 95, 1328-1333] and similar, which enable simultaneous deprotection and cleavage of the compound from the polymeric support.

Cosmetic or Pharmaceutical Compositions of the Invention

The compounds of the invention can be administered by any means that causes contact between the compounds and the site of action in a mammal's body, preferably that of a human being, and in the form of a composition which contains them.

To this regard, another aspect of the invention is a cosmetic or pharmaceutical composition which comprises at least one compound of general formula (I), its stereoisomers, mixtures thereof, and/or its cosmetically or pharmaceutically acceptable salts together with at least one cosmetically or pharmaceutically acceptable adjuvant or excipient. These compositions can be prepared by conventional means known to persons skilled in the art ["*Harry's Cosmeticology*", Seventh edition, (1982), Wilkinson J. B., Moore R. J., ed. Longman House, Essex, GB].

The compounds of this invention have variable solubility in water, according to the nature of their amino acid sequences or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically or pharmaceutically effective amount of the compounds of the invention which should be administered, as well as their dosage, will depend on numerous factors, including age, state of the patient, the nature or severity of the condition, disorder or disease to be treated and/or cared for, the route and frequency of administration and of the particular nature of the compounds to be used.

"Cosmetically and pharmaceutically effective amount" is understood to mean a non-toxic but sufficient amount of the compound or compounds of the invention to provide the desired effect. The compounds of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.00001% (in weight) and 10% (in weight) and even more preferably between 0.0001% (in weight) and 5% (in weight).

The compounds of general formula (I), their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compounds of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports, for example and not restricted to, talc, bentonite, silica, starch or maltodextrin among others.

The compositions which contain the compounds of general formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body. Preferably, the fabrics, non-woven fabrics and medical devices containing the compounds of the invention are used for the treatment and/or care of conditions, disorders and/or diseases which improve or are prevented by the inhibition of cytokine release, the inhibition of the matrix metalloproteinases activity and/or the inhibition of melanogenesis.

Examples of fabrics, non-woven fabrics, garments, medical devices and means for immobilizing the compounds to them, among which are the delivery systems and/or the sustained release systems described above, can be found in literature and are known in the prior art [Schaab C. K. (1986) HAPPI May 1986; Nelson G., "*Application of microencapsulation in textiles*", *Int. J. Pharm.*, (2002), 242(1-2), 55-62; "*Biofunctional Textiles and the Skin*" *Curr. Probl. Dermatol.* (2006), v. 33, Hipler U. C. and Elsner P., eds. S. Karger A G, Basel, Switzerland; Malcolm R. K. et al., "*Controlled release of a model antibacterial drug from a novel self-lubricating silicone biomaterial*", *J. Cont. Release*, (2004), 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions of topical or transdermal application which optionally include cosmetically or pharmaceutically acceptable excipients necessary for formulating the desired administration form. A person skilled in the art knows the different excipients which can be used in the cosmetic or pharmaceutical compositions which contain the compounds of the invention.

The compositions of topical or transdermal application can be produced in any solid, liquid or semisolid formulation, for example and not restricted to, creams, multiple emulsions, for example and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories, for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the compounds of the invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the compound of the invention. The application area will be determined by the nature of the condition, disorder and/or disease to be treated or prevented.

Furthermore, the cosmetic or pharmaceutical compositions containing the compounds of general formula (I), their stereoisomers, mixtures thereof and/or their cosmetically or pharmaceutically acceptable salts can be used in different types of formulations for oral administration, preferably in the form of oral cosmetics or drugs, for example and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, for example and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the compounds of general formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to, other agents inhibiting cytokine release, other agents inhibiting matrix metalloproteinases, other whitening or depigmenting agents, other melanin synthesis inhibiting agents, other anti-inflammatory and/or analgesic agents, other anti-itching agents, other antiangiogenic agents, other anti-reddening agents, agents that inhibit vascular permeability, venotonic agents, agents acting on capillary circulation and/or microcirculation, calming agents, other sunscreens and organic or mineral photoprotective agents active against ultraviolet A and/or B rays and/or infrared A rays, agents that inhibit serine proteases such as kallikreins, leukocyte elastase or cathepsin G, agents stimulating melanocyte proliferation, agents for the treatment and/or care of sensitive skin, agents modulating PPARγ, agents inhibiting neuronal exocytosis, agents inhibiting muscular contraction, antiaging agents, anti-wrinkle agents, antiperspirant agents, anesthetic agents, inhibitors of acetylcholine-receptor aggregation, anticholinergic agents, melanin synthesis stimulating agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or delaying their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, AQP-3 modulating agents, aquaporin synthesis-stimulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents stimulating the synthesis of lipids and components of the stratum corneum, ceramides, fatty acids, agents that inhibit collagen degradation, agents that inhibit elastin degradation, agents stimulating fibroblast proliferation, agents stimulating keratinocyte proliferation, agents stimulating adipocyte proliferation, agents stimulating keratinocyte differentiation, agents stimulating or delaying adipocyte differentiation, agents inhibiting acetylcholinesterase, skin relaxant agents, antihyperkeratosis agents, comedolytic agents, anti-psoriatic agents, DNA repair agents, DNA protecting agents, stabilizers, firming agents, anti-stretch mark agents, binding agents, agents regulating sebum production, lipolytic agents or agents stimulating lipolysis, adipogenic agents, agents modulating PGC-1α, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents stimulating angiogenesis, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor-masking deodorants, chelating agents, plant extracts, essential oils, marine extracts, agents obtained from a biotechnological process, mineral salts, cell extracts, or mixtures thereof, provided they are physically and chemically compatible with the rest of components of the composition and in particular with the compounds of the invention. Furthermore, the nature of said additional ingredients should not unacceptable alter the benefits of the compounds of this invention. The nature of said additional ingredients can be synthetic or natural, such as plant extracts, or come from a biotechnological procedure or from a combination of a synthetic procedure and biotechnological procedure. Additional examples are described in *CTFA International Cosmetic Ingredient Dictionary & Handbook,* 12*th Edition* (2008). In the context of this invention, biotechnological procedure is understood to be any procedure that produces the active ingredient, or part of it, in an organism, or in part of it.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one extract, one synthetic compound or product of biotechnological origin that is an anti-wrinkle and/or antiaging agent, is selected, for example and not restricted to, the group formed by the extracts or hydrolyzed extracts of *Vitis vinifera, Rosa canina, Curcuma longa, Theobroma cacao, Ginkgo biloba, Leontopodium alpinum* or *Dunaliella salina,* among others; Matrixyl® [INCI: Palmitoyl Pentapeptide-4], Matrixyl 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: Calcium Hydroxymethionine], Renovage [INCI: Teprenone], Resistem™ [INCI: *Globularia Cordifolia* Ferment] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen® [INCI: *Glycine Soja* (Soybean) Protein, Oxido Reductases] marketed by Pentapharm/DSM, Myoxinol™ [INCI: Hydrolyzed Hibiscus *Esculentus* Extract], Syniorage™ [INCI: Acetyl Tetrapeptide-11], Dermican™ [INCI: Acetyl Tetrapeptide-9] or DN AGE™ LS [INCI: *Cassia Alata* leaf Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolized Wheat Protein, Hydrolized Soy Protein, Tripeptide-1], Preventhelia™ [INCI: Diaminopropionoyl Tripeptide-33], Decorinyl® [INCI: Tripeptide-10 Citrulline], Decorinol® [INCI: Tripeptide-9 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyl Tetrapeptide-22], Lipochroman™ [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide 10 Citrulline], Hyadisine™ [INCI: *Pseudoalteromonas* Ferment Extract], Hyanify™ [proposed INCI: Saccharide Isomerate], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™ [INCI: Acetyl Hexapeptide-38] marketed by Lipotec, Kollaren® [INCI: Tripeptide-1, Dextran] marketed by Institut Europeen de Biologie Cellulaire/Unipex Innovations, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: Acmella *Oleracea* Extract], Gatuline® In-Tense [INCI: Spilanthes *Acmella* Flower Extract] or Gatuline® Age Defense 2 [INCI: *Juglans Regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium/Unipex Innovations, EquiStat [INCI: *Pyrus* Malus Fruit Extract, *Glycine Soja* Seed Extract] or Juvenesce [INCI: Ethoxydiglicol and Caprylic Triglyceride, Retinol, Ursolic Acid, Phytonadione, Ilomastat] marketed by Coletica/Engelhard/BASF, Ameliox [INCI: Carnosine, Tocopherol, *Silybum Marianum* Fruit Extract] or PhytoCellTec *Malus Domestica* [INCI: *Malus Domestica* Fruit Cell Culture] marketed by Mibelle Biochemistry, Bioxilift [INCI: Pimpinella Anisum Extract] or SMS Anti-Wrinkle® [INCI: Annona *Squamosa* Seed Extract] marketed by Silab, antagonists of the $Ca^{2+}$ channel, for example and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repairing enzymes, for example and not restricted to, photolyase or T4 endonuclease V, or chloride channel agonists, among others.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one natural extract or essential oil that is an anti-itching agent, for example and not restricted to, extracts of *Abelmoschus esculentus, Actaea alba, Aglaia odorata, Alkanna tinctoria, Althaea officinalis, Altingia excelsa, Andropogon virginicus, Aralia nudicaulis, Aralia racemosa, Argemone mexicana, Barleria prionitis, Camelia sinensis, Caesalpinia digyna, Campsis grandiflora, Carissa congesta, Carthamus oxyacantha, Cassia tora, Chrysanthemum indicum, Cimicifuga racemosa, Cinnamomum camphora, Clematis vitalba, Cuscuta reflexa, Diospyros peregrina, Enicostema axillare, Hammamelis virginiana, Jatropha multifida, Lavandula officinalis, Lavandula latifolia, Liquidambar orientalis, Lithospermum officinale, Madhuca longifolia, Martynia annua, Medicago sativa, Michelia champaca, Mikania glomerata, Mimosa pudica, Oryza sativa, Phaseolus vulgaris, Phyllanthus urinaria, Phyllanthus virgatus, Pistacia vera, Polygonum hydropiper, Quercus ilex, Rauvolfia caffra, Ricinus communis, Rubus idaeus, Sagittaria sagittifolia, Sandoricum koetjape, Sapindus mukorossi, Schleichera oleosa, Sesbania grandiflora, Spondias dulcis, Tilia* sp., *Toona ciliata, Tragia involucrata, Trichosanthes quinquangulata, Vaccaria pyramidata, Ventilago madraspatana, Veratrum album* or *Xanthium strumarium*, among others or also at least one synthetic compound or product of biotechnological origin that is an anti-itching agent, for example and not restricted to, mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cyclizine, chlorcyclizine, hydroxyzine, meclizine, cetirizine, levocetirizine, promethazine, thenaldine, alimemazine (trimeprazine), cyproheptadine, azatidine, ketotifen, acrivastine, astemizole, cetirizine, loratadine, desloratadine, mizolastine, terfenadine, fexofenadine, azelastine, levocabastine, olopatadine, corticosteroids such as cortisone, hydrocortisone, dexamethasone, prednisone; Neutrazen™ [INCI: Water, Butylene Glycol, Dextran, Palmitoyl Tripeptide-8] marketed by Atrium/Unipex Innovations, Meliprene® [INCI: Dextran, Acetyl Heptapeptide-1] marketed by Institut Européen de Biologie Cellulaire/Unipex Innovations, Delisens™ [INCI: Acetyl Hexapeptide-46] marketed by Lipotec, Skinasensyl™ [INCI: Acetyl Tetrapeptide-15] marketed by Laboratoires Sérobiologiques/Cognis/BASF, SymSitive® 1609 [INCI: 4-t-Butylcyclohexanol] marketed by Symrise, Symbiocell™ [INCI: Extract from Cestrum *Latifolium*] marketed by BASF, Gatuline® Derma-Sensitive [INCI: Octyldodecyl Myristate, Capparis *Spinosa* Fruit Extract] marketed by Gattefossé or MAXnolia [INCI: *Magnolia Officinalis* Bark Extract, *Vitis Vinifera/Vitis Vinifera* (Grape) Seed Extract, Tocopherol] marketed by Mibelle Biochemistry, among others or mixtures thereof.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one anti-inflammatory agent and/or analgesic selected, for example and not restricted to, from the group formed by extract of madecassoside, extract of *echinacea*, amaranth seed oil, sandal wood oil, extract of peach tree leaf, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca altemifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, non-steroidal anti-inflammatories including cyclooxygenase or lipoxygenase inhibitors, benzydamine, acetylsalicylic acid, rosmarinic acid, ursolic acid, glycyrrhizinate derivatives, α-bisabolol, azulene and analogs, sericoside, ruscogenin, escin, escholine, rutin and analogs, hydrocortisone, clobetasol, dexamethasone, halobetasol, diflorasone, fluocinonide, amcinonide, triamcinolone, fluticasone, fluocinolone, flurandrenolide, prednicarbate, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, buprenorphine, benzocaine, lidocaine, chloroprocaine, tetracaine, procaine, amitriptyline, carbamazepine, gabapentin, pregabalin, bisabolol, Neutrazen™ [INCI: Water, Butylene Glycol, Dextran, Palmitoyl Tripeptide-8] marketed by Atrium/Unipex Innovations, Delisens™ [proposed INCI: Acetyl Hexapeptide-46] marketed by Lipotec, Meliprene® [INCI: Dextran, Acetyl Heptapeptide-1] marketed by Institut Européen de Biologie Cellulaire/Unipex Innovations, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Sérobiologiques/Cognis/BASF, Calmosensine™ [INCI: Acetyl Dipeptide-1] marketed by Sederma, coenzyme Q10 or alkyl glycerol ethers, among others, or mixtures thereof.

Another aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one whitening or depigmenting agent, for example and not restricted to, the extracts of *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria Galericulate, Sedum sarmentosum Bunge, Stellaria medica, Triticum Vulgare, Uva ursi* or *Whitania somnifera*, among others, and/or a cosmetically or pharmaceutically effective quantity of at least one synthetic compound, extract or product from a biofermentation process with depigmenting activity, for example and not restricted to Lipochroman™ 6 [INCI: Dimethylmethoxy Chromanol], Chromabright™ [INCI: Dimethylmethoxy Chromanyl Palmitate], marketed by Lipotec, Actiwhite™ LS9808 [INCI: Aqua, Glycerin, Sucrose Dilaurate, Polysorbate 20, *Pisum sativum* (Pea) extract] or Dermawhite® NF LS9410 [INCI: Mannitol, Arginine HCl, Phenylalanine, Disodium EDTA, Sodium Citrate, Kojic Acid, Citric Acid, Yeast Extract] marketed by Laboratoires Sérobiologiques/Cognis/BASF, Lumiskin™ [INCI: Caprylic/Capric Triglycerid, Diacetyl-Boldine], Melaclear™ [INCI: Glycerin, Aqua, Dithiaoctanediol, Gluconic acid, Sutilains, Beta-carotene] or Etioline™ [INCI: Glycerin, Butylene Glycol, *Arctostaphylos uva ursi* Leaf Extract, *Mitracarpus scaber* Extract] marketed by Sederma/Croda, Sepiwhite™ MSH [INCI: Undecylenoyl Phenylalanine] marketed by Seppic, Achromaxyl [INCI: Aqua, *Brassica napus* Extract] marketed by Vincience/ISP/Ashland, Gigawhite™ [INCI: Aqua, Glycerin, *Malva sylvestris* (Mallow) Extract, *Mentha piperita* Leaf Extract, *Primula veris* Extract, *Alchemilla vulgaris* Extract, *Veronica officinalis* Extract, *Melissa officinalis* Leaf Extract, *Achillea millefolium* Extract], Melawhite® [INCI: Leukocyte Extract, AHA] or Melfade®-J [INCI: Aqua, *Arctostaphylos uva-ursi* Leaf Extract, Glycerin, Magnesium Ascorbyl Phosphate] marketed by Pentapharm/DSM, Albatin® [INCI: Aminoethylphosphoric Acid, Butylene Glycol, Aqua] marketed by Exsymol, Tyrostat™-11 [INCI: Aqua, Glycerin, *Rumex occidentalis* Extract] or Melanostatine®-5 [INCI: Dextran, Nonapeptide-1] marketed by Atrium/Unipex Innovations, arbutin and its isomers, kojic acid and its derivatives, vitamin C and its derivatives, for example and not restricted to, 6-O-palmitoylascorbic acid, dipalmitoylascorbic acid, magnesium salt from ascorbic-2-phosphate acid (MAP), sodium from ascorbic-2-phosphate acid (NAP), ascorbyl glucoside or ascorbyl tetraisopalmitate (VCIP) among others, retinol and its derivatives, including tretinoin and isotretinoin, idebenone, hydroxybenzoic acid and its derivatives, flavonoides, soy extract, extract of lemon, extract of orange, extract of *ginkgo*, extract of cucumber, extract of geranium, extract of bearberry, extract of carob, extract of cinnamon, extract of marjoram, extract of rosemary, extract of clove, soluble extract of licorice, extract of blackberry leaf, niacinamide, liquiritin, resorcinol and its derivatives, hydroquinone, α-tocopherol, γ-tocopherol, azelaic acid, resveratrol, mercury salts, linoleic acid, α-lipoic acid, dihydrolipoic acid, alpha hydroxy acids, beta hydroxy acids, ellagic acid, ferulic acid, cinnamic acid, oleanolic acid, aloesin and its derivatives, PAR-2 inhibitors and/or serine protease inhibitors, for example and not restricted to, tryptase, trypsin or kallikrein inhibitors, among others.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one agent inhibiting matrix metalloproteinases, for example and not restricted to, ursolic acid, isoflavones such as genistein, quercetin, carotenoids, lycopene, extract of soybean, extract of cranberry, extract of rosemary, extract of *Trifolium pratense* (red clover), extract of *Phormium tenax* (*phormium*), extract of kakkon-to, extract of sage, retinol and its derivatives, retinoic acid and its derivatives, sapogenins such as diosgenin, hecogenin, smilagenin, sarsapogenin, tigogenin, yamogenin and yucagenin, among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI: *Pyrus Malus* Fruit Extract, *Glycine Soja* Seed Extract] marketed by Coletica/Engelhard/BASF, Pepha®-Timp [INCI: Human Oligopeptide-20], Regu-Age [INCI: Hydrolyzed Rice Bran Protein, *Glycine Soja* Protein, Oxido Reductases] or Colhibin [INCI: Hydrolyzed Rice Protein] marketed by Pentapharm/DSM, Lipeptide [INCI: Hydrolized Vegetable Protein] or Peptide AC29 [INCI: Acetyl Tripeptide-30 Citrulline] marketed by Lipotec, Litchiderm™ [INCI: Litchi *Chinensis* Pericarp Extract] or Arganyl™ [INCI: Argania *Spinosa* Leaf Extract] marketed by Laboratoires Sérobiologiques/Cognis/BASF, MDI Complex® [INCI: Glycosaminoglycans] or ECM-Protect® [INCI: Water (Aqua), Dextran, Tripeptide-2] marketed by Atrium/Unipex Innovations, Dakaline [INCI: *Prunus Amygdalus Dulcis*, Anogeissus Leiocarpus Bark Extract] marketed by Soliance, Homeostatine [INCI: Enteromorpha *Compressa, Caesalpinia Spinosa*] marketed by Provital, Timp-Peptide [proposed INCI: Acetyl Hexapeptide] or ECM Moduline [proposed INCI: Palmitoyl Tripeptide] marketed by Infinitec Activos, IP2000 [INCI: Dextran, Trifluoroacetyl Tripeptide-2] marketed by Institut Europeen de Biologie Cellulaire/Unipex Group, Actimp 1.9.3° [INCI: Hydrolyzed Lupine Protein] marketed by Expanscience Laboratories, Vitaderm® [INCI: Alcohol, Water (Aqua), Glycerin, Hydrolyzed Rice Protein, Ilex *Aquifolium* Extract, Sodium Ursolate, Sodium Oleanolate] marketed by Rahn, adapalene, tetracyclines and its derivatives such as minocycline, rolitetracycline, chlortetracycline, metacycline, oxytetracycline, doxycycline, demeclocycline and its salts, Batimastat [BB94; [4-(N-hydroxyamino)-2R-isobutyl-3S-(thiophene-2-ylthiomethyl)succinyl]-L-phenylalanine-N-methylamide], Marimastat [BB2516; [2S—[N-4(R*),2R*,3S]]—N-4 [2,2-dimethyl-1-[methylaminocarbonyl]propyl]-N1, 2-dihydroxy-3-(2-methyl-propyl) butanediamide], among others.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one extract, one synthetic compound or product of biotechnological origin which is an agent that acts on capillary circulation and/or microcirculation, agent that inhibits vascular permeability, venotonic agent or an anti-redness agent, for example and not restricted to, extracts or hydrolized extracts of *Tambourissa trichophylla, Tambourissa microphylla, Tambourissa religiose, Tambourissa capuronii*, Phytotonine [INCI: Propylene Glycol, *Arnica Montana* (Flower) Extract, *Cupressus Sempervirens* (Seed) Extract, *Polygonatum Multiflorum* Extract], Haloxyl [INCI: Hydroxysuccinimide, Chrysin, Palmitoyl Oligopeptide, Palmitoyl Tetrapeptide-7] or Eye-Liss [INCI: Hesperidin Methyl Chalcone, Dipeptide-2, Palmitoyl Tetrapeptide-7] marketed by Sederma/Croda, Regu-CEA [INCI: Spent Grain Wax, Isomerized Linoleic Acid, Behenic Acid, Palmitoyl Tripeptide-5] or Regu-AGE [INCI: Hydrolyzed Rice Bran Protein, *Glycine Soja* Protein] marketed by Pentapharm/DSM, Biophytex [INCI: Water, Butylene Glycol, Panthenol, Escin, Glycerin, *Ruscus Aculeatus* Root Extract, Ammonium Glycyrrhizate, Centella *Asiatica*, Extract, Hydrolyzed Yeast Protein, *Calendula Officinalis* Flower Extract] marketed by Laboratoires Sérobiologiques/Cognis/BASF, Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Liporeductyl® [INCI: Water, Glycerin, Lecithin, Caffeine, Butcherbroom (*Ruscus Aculeatus*) Root Extract, Maltodextrin, Silica, Tea-Hydroiodide, Propylene Glycol, Ivy (*Hedera Helix*) Extract, Carnitine, Escin, Tripeptide-1, Xanthan Gum, Carrageenan (*Chondrus Crispus*), Disodium EDTA], or Delisens™ [proposed INCI: Acetyl Hexapeptide-46] marketed by Lipotec, MDI Complex [INCI: Glycosaminoglycans] marketed by Atrium/Unipex Innovations, IsoSlim Complex [INCI: Soy Isoflavones, Caffeine, Carnitine, *Spirulina Platensis* Extract, Polysorbate 80, Alcohol, Phenoxyethanol, Aqua] marketed by Mibelle Biochemistry, Eye Regener [INCI: Water, *Medicago Sativa* (Alfalfa) Seed Extract, Hydrolyzed Lupine Protein] marketed by Silab, IBR-CalmDeAge [INCI: Glycerin, Water, *Phoenix Dactylifera* (Dale) Seed Extract] marketed by IBR, Concentrate Coralline [INCI: Water, *Corallina Officinalis* Extract, Propylene Glycol, Phenoxyethanol, Chlorphenesin, Methylparaben] or Rhodofiltrat *Delesseria* HG [INCI: Dipropylene Glycol, Aqua, *Delesseria Sanguinea* Extract] marketed by Codif, Silidine [INCI: Porphyridium cruentum exsudate] marketed by Greentech, Legactif [INCI: Glycerin, Aqua, *Ruscus Aculeatus* Root Extract, *Citrus Limon* Peel Extract, *Solidago Virgaurea* Extract] marketed by Provital, among others, or mixtures thereof.

Another aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one bacteriostatic and/or bactericide agent and/or a fungistatic and/or fungicide agent, for example and not restricted to, caprylyl glycol, imidazolidinyl urea, methyl 4-hydroxybenzoate [INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropan-1,3-diol, 3-p-chlorophenoxy-1,2-propanediol (chlorphenesin), dichlorobenzyl alcohol, iodopropynyl butylcarbamate, benzalkonium chloride, benzetonium chloride, chlorhexidine, ethanol, isopropanol, methanol, 1,2-hexanodiol, 1,2-octanodiol, pentylene glycol, glyceryl laurate, glyceryl caprylate, glyceryl caprate, benzoyl peroxide, chlorhexidine gluconate, triclosan, phenoxyethanol, terpinen-4-ol, α-terpineol, resorcinol, stiemycin, erythromycin, neomycin, clindamycin and its esters, tetracyclines, metronidazole, azelaic acid, tolnaftate, nystatin, clotrimazole, ketoconazole, zinc pyrithione, zinc oxide, isothiazolinones, selenium sulfide, benzyl hemiformal, boric acid, sodium borate, 6,6-dibromo-4,4-dichloro-2,2'-methylene diphenol (bromochlorophenol), 5-bromo-5-nitro-1,3-dioxane, tosylchloramide sodium (Chloramine T), chloroacetamide, p-chloro-m-cresol, 2-benzyl-4-chlorophenol (chlorophenol), dimethyl oxazolidine, dodecyl dimethyl-2-phenoxyethyl ammonium bromide (domiphen bromide), 7-ethyl bicyclic oxazolidine, glutaraldehyde, N-(4-chlorophenyl)-N-[4-chloro-3-(trifluoromethyl)phenyl]-urea (halocarbon), hexetidine, 2-hydroxy-4- isopropyl-2,4,6-cycloheptatriene-1-one (hinokitiol), isopropylmethylphenol, mercury salts, aluminium salts, nisin, phenoxyisopropanol, o-phenylphenol, 3-heptyl-2-[(3-heptyl-4-methyl-3H-thiazole-2-ylidene)methyl]-4-methyl-thiazole iodine (Quaternium-73), silver chloride, sodium iodide, thymol, undecylenic acid, diethylenetriaminepentaacetic acid, ethylenediaminetetraacetic acid, lactoperoxidase, glucose oxidase, lactoferrin and/or a cosmetically or pharmaceutically effective quantity of at least one natural extract or essential oil with intrinsic bactericide, bacteriostatic and/or fungicide activity, for example and not restricted to, the extracts of *Allium sativum, Calendula officinalis, Chamomilla recutita, Echinacea Purpura, Hyssopus Officinalis, Melaleuca alternifolia* or tea tree oil, among others.

An additional aspect of this invention refers to a cosmetic or pharmaceutical composition which comprises a cosmetically or pharmaceutically effective quantity of at least one compound of the invention, its stereoisomers, mixtures thereof and/or its cosmetically or pharmaceutically acceptable salts, as well as a cosmetically or pharmaceutically effective quantity of at least one extract, which stimulates the synthesis of defensins, for example and not restricted to, extracts or hydrolyzed extracts of *Aloe vera, Roast amaranth, Rehmannias radix, arnica, gardenia*, carrot, orange, peach, pineapple, mint, gentian, hibiscus flower, walnut flower, pumpkin, peony, *quinoa*, boldo, sarsaparille, sunflower, elderberry, seaweed, hydrolyzed maize, hydrolyzed soybean or hydrolyzed rice, among others and/or a cosmetically or pharmaceutically effective quantity of at least one synthetic compound, extract or product from a biofermentation process with stimulatory effect on the expression of the defensins, for example and not restricted to, isoleucine and its isomers and derivatives, valine and its isomers and derivatives, calcium and its salts, α-MSH and fragments contained in the sequence of α-MSH amino acids, vitamin A and its derivatives and precursors, vitamin D3 and its derivatives, jasmonic acid, fumaric acid, malic acid, citric acid, ascorbic acid, lactic acid, acetic acid, adipic acid, tartaric acid, cinnamic acid, glutamic acid, succinic acid, inulin, poly-D-glutamic acid, glycine, L-methionine, L-alanine, L-citrulline, lactoprotein, casein, lactoperoxidase, lysozyme, polyphenol, extract of *Lactobacillus*, extract of fusobacteria or non-photosynthetic and non-fructifying filamentous bacteria, Bodyfensine [INCI: Acetyl Dipeptide-3 Aminohexanoate], among others.

An additional aspect of this invention refers to a cosmetic or pharmaceutical composition which comprises a cosmetically or pharmaceutically effective quantity of at least one compound of general formula (I), its stereoisomers, mixtures thereof and/or its cosmetically or pharmaceutically acceptable salts, as well as a cosmetically or pharmaceutically effective quantity of at least one agent for the treatment of rosacea, for example and not limited to, Regu®-CEA [INCI: Spent Grain Wax, Isomerized Linoleic Acid, Behenic Acid, Palmitoyl Tripeptide-5] or Regu®-AGE [INCI: Hydrolyzed Rice Bran Protein, Oxido Reductases, *Glycine Soja* (Soybean) Protein] marketed by DSM, Biophytex™ [INCI: Escin, *Ruscus Aculeatus* Root Extract, Ammonium Glycyrrhizate, *Centella Asiatica* Extract, Hydrolyzed Yeast Protein, *Calendula Officinalis* Flower Extract] marketed by Laboratoires Sérobiologiques, MDI Complex® [INCI: Glycosaminoglycans] marketed by Unipex, Phytotonine™ [INCI: *Arnica Montana* (Flower) Extract, *Cupressus Sempervirens* (Seed) Extract, *Polygonatum Multiflorum* Extract], Haloxyl™ [INCI: Hydroxysuccinimide, Chrysin, Palmitoyl Oligopeptide, Palmitoyl Tetrapeptide-7] or Eye-Liss™ [INCI: Hesperidin Methyl Chalcone, Dipeptide-2, Palmitoyl Tetrapeptide-7] marketed by Sederma, IBR-Calm-DeAge™ [INCI: Glycerin, Water, *Phoenix Dactylifera* (Dale) Seed Extract] marketed by IBR, Concentrate Coralline [INCI: Water, *Corallina Officinalis* Extract, Propylene Glycol, Phenoxyethanol, Chlorphenesin, Methylparaben] or Rhodofiltrat *Delesseria* HG [INCI: Dipropylene Glycol, Aqua, *Delesseria Sanguinea* Extract] marketed by Codif, Silidine® [INCI: Porphyridium cruentum exsudate] marketed by Greentech, Eye Regener [INCI: Water, *Medicago Sativa* (Alfalfa) Seed Extract, Hydrolyzed Lupine Protein] marketed by Silab, IsoSlim Complex [INCI: Soy Isoflavones, Caffeine, Carnitine, *Spirulina Platensis* Extract, Polysorbate 80, Alcohol, Phenoxyethanol, Aqua] marketed by Mibelle, Legactif [INCI: Glycerin, Aqua, *Ruscus Aculeatus* Root Extract, *Citrus Limon* Peel Extract, *Solidago Virgaurea* Extract] marketed by Provital, antibiotics such as tetracycline, minocycline, erythromycin, doxycycline or azithromycin, anti-infective agents such as azelaic acid, nadifloxacin, sodium sulfacetamide and metronidazole, anti-inflammatories with folic acids, nicotinamide and zinc oxide, keratolytics such as benzoyl peroxide, resorcinol and salicylic acid and retinoids.

Applications

In another aspect, this invention refers to a compound of general formula (I),

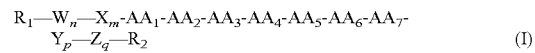

its stereoisomers, mixtures thereof and/or its cosmetically or pharmaceutically acceptable salts, wherein AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from and have a value of 0 or 1;
n+m+p+q is smaller or equal to 2;
with the condition that if AA$_1$ is a bond, AA$_2$ is -Ala-, AA$_4$ is -Val- and AA$_6$ is a bond, then AA$_5$ is -Thr-;
with the condition that if AA$_1$ is a bond, AA$_2$ is -Val-, AA$_3$ is -Thr-, AA$_4$ is -Val- and AA$_6$ is a bond, then AA$_5$ is -Ala-;
with the condition that if AA$_1$ is a bond, AA$_2$ is -Val-, AA$_3$ is -Thr-, AA$_4$ is -Asn-, AA$_5$ is -Ala- and AA$_6$ is a bond, then n+m+p+q is equal to 0;
with the condition that if AA$_1$ is a bond, AA$_2$ is -Ala-, AA$_3$ is -Thr-, AA$_4$ is -Val-, AA$_6$ is a bond and p+q is greater or equal to 1, then AA$_5$ is -Ala-;
with the condition that if AA$_1$ is a bond, AA$_2$ is -Ala-, AA$_3$ is -Thr-, AA$_4$ is -Asn-, AA$_5$ is -Thr- and AA$_6$ is a bond, then n+m+p+q is smaller or equal to 1;
with the condition that if AA$_1$ is a bond, AA$_2$ is -Val-, AA$_3$ is -Thr-, AA$_4$ is -Val-, AA$_5$ is -Ala-, AA$_6$ is a bond, then p and q are 0;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;

R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and R$_1$ or R$_2$ are not α-amino acids for its use in medicine.

In another aspect, this invention refers to a compound of general formula (I),

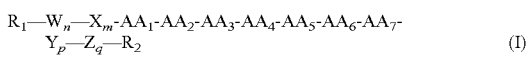
R$_1$—W$_n$—X$_m$-AA$_1$-AA$_2$-AA$_3$-AA$_4$-AA$_5$-AA$_6$-AA$_7$-
Y$_p$—Z$_q$—R$_2$     (I)

its stereoisomers, mixtures thereof and/or its cosmetically or pharmaceutically acceptable salts, wherein AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
with the condition that if AA$_1$ is a bond, AA$_2$ is -Val-, AA$_3$ is -Thr-, AA$_4$ is -Val-, AA$_5$ is -Ala-, AA$_6$ is a bond, then p and q are 0;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R$_1$ or R$_2$ are not α-amino acids, for the treatment of the skin and/or mucous membranes.

In another aspect, this invention refers to the use of a compound of general formula (I),

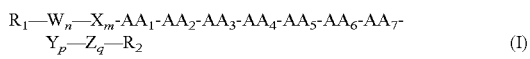
R$_1$—W$_n$—X$_m$-AA$_1$-AA$_2$-AA$_3$-AA$_4$-AA$_5$-AA$_6$-AA$_7$-
Y$_p$—Z$_q$—R$_2$     (I)

its stereoisomers, mixtures thereof and/or its cosmetically or pharmaceutically acceptable salts, wherein AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R$_1$ or R$_2$ are not α-amino acids, for the cosmetic, non-therapeutic, treatment and/or care of the skin and/or mucous membranes, in particular for the treatment, prevention, and/or care of aging and/or photoaging, treatment, prevention, and/or care of wrinkles and/or expression wrinkles and/or the treatment and/or care of spots due to aging and/or photoaging.

In another aspect, this invention refers to the use of a compound of general formula (I),

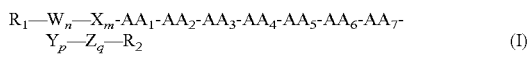
R$_1$—W$_n$—X$_m$-AA$_1$-AA$_2$-AA$_3$-AA$_4$-AA$_5$-AA$_6$-AA$_7$-
Y$_p$—Z$_q$—R$_2$     (I)

its stereoisomers, mixtures thereof and/or its cosmetically or pharmaceutically acceptable salts, wherein AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;

with the condition that if $AA_1$ is a bond, $AA_2$ is -Val-, $AA_3$ is -Thr-, $AA_4$ is -Val-, $AA_5$ is -Ala-, $AA_6$ is a bond, then p and q are 0;

$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and $R_1$ or $R_2$ are not α-amino acids, for its use in the treatment of pain, inflammation, itching, angiogenic disorders and/or diseases of the skin and/or pigmentation disorders and/or diseases.

In another aspect, this invention refers to a compound of general formula (I),

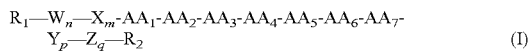

its stereoisomers, mixtures thereof and/or its cosmetically or pharmaceutically acceptable salts, wherein $AA_1$ is selected from the group formed by -Ser- and bond;
$AA_2$ is selected from the group formed by -Val- and -Ala-;
$AA_3$ is selected from the group formed by -Arg- and -Thr-;
$AA_4$ is selected from the group formed by -Val- and -Asn-;
$AA_5$ is selected from the group formed by -Ala- and -Thr-;
$AA_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and $R_1$ or $R_2$ are not α-amino acids, for its use in the inhibition of cytokine release. Preferably, cytokines are interleukins. More preferably, interleukins are interleukin IL6 and IL8 whose release is mediated by peptide LL-37.

In another aspect, this invention refers to a compound of general formula (I),

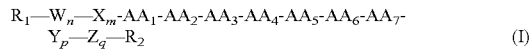

its stereoisomers, mixtures thereof and/or its cosmetically or pharmaceutically acceptable salts, wherein $AA_1$ is selected from the group formed by -Ser- and bond;
$AA_2$ is selected from the group formed by -Val- and -Ala-;
$AA_3$ is selected from the group formed by -Arg- and -Thr-;
$AA_4$ is selected from the group formed by -Val- and -Asn-;
$AA_5$ is selected from the group formed by -Ala- and -Thr-;
$AA_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and $R_1$ or $R_2$ are not α-amino acids, for its use in the inhibition of matrix metalloproteinases activity. Preferably, the matrix metalloproteinase is collagenase.

In another aspect, this invention refers to a compound of general formula (I),

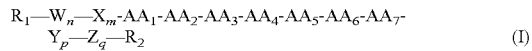

its stereoisomers, mixtures thereof and/or its cosmetically or pharmaceutically acceptable salts, wherein $AA_1$ is selected from the group formed by -Ser- and bond;
$AA_2$ is selected from the group formed by -Val- and -Ala-;
$AA_3$ is selected from the group formed by -Arg- and -Thr-;
$AA_4$ is selected from the group formed by -Val- and -Asn-;

AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R$_1$ or R$_2$ are not α-amino acids,
for its use in the inhibition of melanogenesis. Preferably, the inhibition of melanogenesis is obtained by inhibition of tyrosinase.

Alternatively, in another aspect, this invention refers to a method of treatment, prevention and/or care of pain, inflammation, itching, angiogenic disorders and/or diseases of the skin and/or pigmentation disorders and/or diseases, which comprises the administration of a cosmetically or pharmaceutically effective quantity of at least one compound of general formula (I),

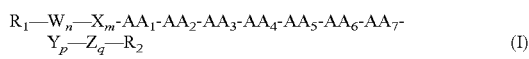

its stereoisomers, mixtures thereof and/or its cosmetically or pharmaceutically acceptable salts, wherein
AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
with the condition that if AA$_1$ is a bond, AA$_2$ is -Val-, AA$_3$ is -Thr-, AA$_4$ is -Val-, AA$_5$ is -Ala-, AA$_6$ is a bond, then p and q are 0;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R$_1$ or R$_2$ are not α-amino acids.

In another aspect, the invention refers to a method of treatment of the skin and/or mucous membranes which comprises the administration of a cosmetically or pharmaceutically effective quantity of at least one compound of general formula (I),

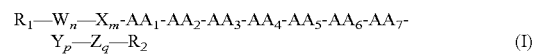

its stereoisomers, mixtures thereof and/or its cosmetically or pharmaceutically acceptable salts, wherein
AA$_1$ is selected from the group formed by -Ser- and bond;
AA$_2$ is selected from the group formed by -Val- and -Ala-;
AA$_3$ is selected from the group formed by -Arg- and -Thr-;
AA$_4$ is selected from the group formed by -Val- and -Asn-;
AA$_5$ is selected from the group formed by -Ala- and -Thr-;
AA$_6$ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
with the condition that if AA$_1$ is a bond, AA$_2$ is -Val-, AA$_3$ is -Thr-, AA$_4$ is -Val-, AA$_5$ is -Ala-, AA$_6$ is a bond, then p and q are 0;
R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R$_2$ is selected from the group formed by —NR$_3$R$_4$, —OR$_3$ and —SR$_3$, wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R$_1$ or R$_2$ are not α-amino acids.

In another aspect, the invention refers to a method of cosmetic, non-therapeutic, treatment and/or care of the skin and/or mucous membranes, that comprises the administration of a cosmetically or pharmaceutically effective quantity of at least one compound of general formula (I),

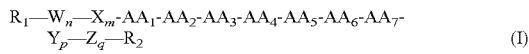

its stereoisomers, mixtures thereof and/or its cosmetically or pharmaceutically acceptable salts, wherein
  $AA_1$ is selected from the group formed by -Ser- and bond;
  $AA_2$ is selected from the group formed by -Val- and -Ala-;
  $AA_3$ is selected from the group formed by -Arg- and -Thr-;
  $AA_4$ is selected from the group formed by -Val- and -Asn-;
  $AA_5$ is selected from the group formed by -Ala- and -Thr-;
  $AA_6$ is selected from the group formed by -Val- and bond;
  W, X, Y, Z are amino acids and are independently selected from amongst themselves;
  n, m, p and q are independently selected from amongst themselves and have a value of 0 or 1;
  n+m+p+q is smaller or equal to 2;
  $R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
  $R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
  $R_1$ or $R_2$ are not α-amino acids.

In another aspect, the invention refers to a method of inhibition of cytokine release that comprises the administration of a cosmetically or pharmaceutically effective quantity of at least one compound of general formula (I),

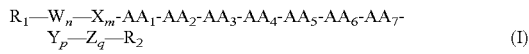

its stereoisomers, mixtures thereof and/or its cosmetically or pharmaceutically acceptable salts, wherein
  $AA_1$ is selected from the group formed by -Ser- and bond;
  $AA_2$ is selected from the group formed by -Val- and -Ala-;
  $AA_3$ is selected from the group formed by -Arg- and -Thr-;
  $AA_4$ is selected from the group formed by -Val- and -Asn-;
  $AA_5$ is selected from the group formed by -Ala- and -Thr-;
  $AA_6$ is selected from the group formed by -Val- and bond;
  W, X, Y, Z are amino acids and are independently selected from amongst themselves;
  n, m, p and q are independently selected from amongst themselves and have a value of 0 or 1;
  n+m+p+q is smaller or equal to 2;
  $R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
  $R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
  $R_1$ or $R_2$ are not α-amino acids.

In another aspect, the invention refers to a method of inhibition of matrix metalloproteinases activity which comprises the administration of a cosmetically or pharmaceutically effective quantity of at least one compound of general formula (I),

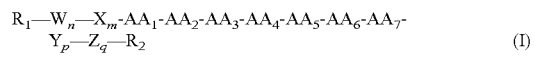

its stereoisomers, mixtures thereof and/or its cosmetically or pharmaceutically acceptable salts, wherein
  $AA_1$ is selected from the group formed by -Ser- and bond;
  $AA_2$ is selected from the group formed by -Val- and -Ala-;
  $AA_3$ is selected from the group formed by -Arg- and -Thr-;
  $AA_4$ is selected from the group formed by -Val- and -Asn-;
  $AA_5$ is selected from the group formed by -Ala- and -Thr-;
  $AA_6$ is selected from the group formed by -Val- and bond;
  W, X, Y, Z are amino acids and are independently selected from amongst themselves;
  n, m, p and q are independently selected from amongst themselves and have a value of 0 or 1;
  n+m+p+q is smaller or equal to 2;
  $R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
  $R_2$ is selected from the group formed by —$NR_3R_4$, —$OR_3$ and —$SR_3$, wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and R₁ or R₂ are not α-amino acids.

In another aspect, the invention refers to a method of inhibition of melanogenesis that comprises the administration of a cosmetically or pharmaceutically effective quantity of at least one compound of general formula (I),

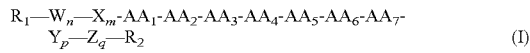

(I)

its stereoisomers, mixtures thereof and/or its cosmetically or pharmaceutically acceptable salts, wherein AA₁ is selected from the group formed by -Ser- and bond;
AA₂ is selected from the group formed by -Val- and -Ala-;
AA₃ is selected from the group formed by -Arg- and -Thr-;
AA₄ is selected from the group formed by -Val- and -Asn-;
AA₅ is selected from the group formed by -Ala- and -Thr-;
AA₆ is selected from the group formed by -Val- and bond;
W, X, Y, Z are amino acids and are independently selected from amongst themselves;
n, m, p and q are independently selected from amongst themselves and have a value of 0 or 1;
n+m+p+q is smaller or equal to 2;
R₁ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R₅—CO—, wherein R₅ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl or substituted or unsubstituted heteroarylalkyl;
R₂ is selected from the group formed by —NR₃R₄, —OR₃ and —SR₃, wherein R₃ and R₄ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl; and
R₁ or R₂ are not α-amino acids.

In accordance with a preferred embodiment, the substituent of the N-terminal end is selected from the group formed by H, a polymer derived from polyethylene glycol and R—CO—, wherein R is selected from the group formed by substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and R—CO— is not an α-amino acid. More preferably, the substituent of the N-terminal end is selected from the group formed by H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, the substituent of the N-terminal end is H, acetyl, lauroyl, myristoyl or palmitoyl. In an even more preferred embodiment, R₁ is acetyl or palmitoyl.

In accordance with another embodiment of this invention, the substituent of the C-terminal end is selected from the group formed by —NR₁R₂, —OR₁, —SR₁, wherein R₁ and R₂ are independently selected from the group formed by H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —NR₁R₂ is not an α-amino acid. Optionally, R₁ and R₂ can be bound by a saturated or unsaturated carbon-carbon bond, forming a cycle with the nitrogen atom. More preferably the substituent of the C-terminal end is —NR₁R₂ or —OR₁. More preferably, R₁ and R₂ are selected from the group formed by H, a polymer derived from polyethylene glycol with a molecular weight comprised between 200 and 35000 Daltons, methyl, ethyl, hexyl, dodecyl and hexadecyl. Even more preferably R₁ is H and R₂ is selected from the group formed by H, methyl, ethyl, hexyl, dodecyl and hexadecyl. In accordance with an even more preferred embodiment, the substituent of the N-terminal end is selected from —OH and —NH₂.

In a preferred embodiment, itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, dermatosis related to pregnancy, dermatosis related to menopause, eczema, sensitive skin, psoriasis, chickenpox, herpes, herpes zoster, Netherton's syndrome, peeling skin syndrome, lichen planus, acne, rosacea, dandruff, seborrhea, seborrheic dermatitis, alopecia, athlete's foot, candidiasis, hemorrhoids, vaginal itching, pruritus ani, anogenital itching, sunburn, urticaria, pruritic otitis, senile pruritus, aquagenic pruritus, prurigo nodularis, prurigo planus, *pityriasis rosea*, xerosis and dry skin, or pruritus associated with dialysis, HIV infection, malignant neoplasms, Hodgkin's disease, leukemia, myeloma, lymphoma, solid tumors, adenocarcinomas, lung cancer, hepatic diseases, jaundice, cholestasis, liver failure, cirrhosis, polycythemia, hypereosinophilic syndrome, essential thrombocythemia, myelodysplastic syndrome, iron-deficiency anemia, systemic erythematosus lupus, endocrine diseases, thyroidal diseases, hyperthyroidism, hypothyroidism, parathyroid diseases, diabetes mellitus, kidney diseases, kidney failure, uremia, parasitic infections, scabies, lice, intestinal worms, allergic reactions, allergies to medication, food allergies, allergies to chemical products, exposure to poisonous plants, exposure to insect bites, chemotherapy, stress and anxiety, among others. Preferably, itching is selected from the group formed by sensitive skin, xerosis, dry skin, dermatitis, psoriasis, acne and rosacea.

In another particular embodiment, pain is selected, for example and not restricted to, from the group formed by acute pain, chronic pain, nociceptive pain, neuropathic pain, inflammatory pain, visceral pain, abdominal pain, digestive system pain, respiratory system pain, urogenital system pain, endocrine system pain, heart pain, pancreatic pain, hepatic pain, pain due to gallstones, cholestasis, intestinal pain, stomach pain, pain due to duodenal ulcers, pain due to esophagitis, pain due to gastroesophageal reflux disease, spleen pain, pain in the blood vessels, thalamic pain syndrome, irritable bowel syndrome, pain associated with Crohn's disease, pain associated with ulcerative colitis, diverticulitis, gastrointestinal mucositis, headaches, tension headaches, headaches associated with sinusitis, migraines, eye pain, dry eye syndrome, postoperative pain, postoperative pain due to surgical incisions, postoperative pain due to implant insertions in the bone, postoperative pain due to bone substitutions, postoperative pain due to infections, postoperative pain due to limb amputations, pain due to bone fractures, pain due to cancer, pain due to bone cancer, pain associated with benign bone tumors, pain associated with osteoid osteomas, pain associated with osteoblastomas, pain due to cancer treatment, pain due to chemotherapy, pain due to emesis, pain due to emesis resulting from chemotherapy treatment, musculoskeletal pain, spastic muscle pain, fibromyalgia, complex regional pain syndrome, psychogenic pain, neuralgic pain, pain due to demyelinating diseases, neck pain associated with cervical dystonia, back pain, lumbago, sciatica, neurogenic inflammation, neuritis, causalgia, touch sensitivity, cold sensitivity, heat sensitivity, skin irritation, post-hair removal skin irritation, post-shaving skin irritation, psoriasis, sensitive skin, dermatitis, atopic dermatitis, contact dermatitis, diaper dermatitis, seborrheic dermatitis, eczema, lichen planus, rosacea, burns, sunburn, arthritis, rheumatoid arthritis, osteoarthritis, psoriatic arthritis, uveitis, pain due to nerve damage, neuralgia, postherpetic neuralgia, neuropathies, peripheral neuropathies, phantom pains, allodynia, hyperalgesia, cold hyperalgesia, pain due to carpal tunnel syndrome, burning pain, Grierson-Gopalan syndrome (better known as burning feet syndrome), burning mouth syndrome, paresthesia, Fabry's disease, facial pain, trigeminal neuralgia, neuropathic pain due to diabetes, neuropathic pain due to AIDS, orofacial pain, dental pain, pain due to tooth removal, pain due to wisdom tooth removal, tooth sensitivity to the cold, tooth sensitivity to heat, oral mucositis, temporomandibular joint pain, joint pain caused by gout, pain associated with tattoo or tattoo removal processes, bunion pain, testicular pain, myofascial pain, urinary bladder pain, urinary tract pain, cystitis, pain due to kidney stones, renal colic, vulval pain, vaginal pain, post-birth pain, menstrual pain, scrotal pain, perineum pain, pelvic pain or hypersensitivity, skin pain or irritation after surgery, after treatment with intense pulsed light therapy (IPL), after treatment with monochromatic pulsed light therapy (laser), after treatment with chemical peeling agents or after overexposure to aggressive external agents and pain due to chronic alcohol abuse.

In another particular aspect, the inflammation is selected, for example and not restricted to, from the group formed by neurogenic inflammation, joint inflammation, tendon inflammation, muscular inflammation, sepsis, vascular inflammation, respiratory inflammation, chronic obstructive pulmonary disease, rhinitis, allergic rhinitis, asthma, otitis, intestinal inflammation, Crohn's disease, pancreatitis, hepatitis, conditions related to chronic inflammation, acute inflammation, nephritis, systemic lupus erythematosus, arthritis, rheumatoid arthritis, adult and juvenile rheumatoid arthritis, Still's disease, psoriatic arthritis, osteoarthritis, arthritis caused by gout, rheumatoid spondylitis, glomerulonephritis, neuritis, nerve tissue inflammation, multiple sclerosis, immune system disorders, Sjögren's syndrome, atherosclerosis, myocarditis, pericarditis, vasculitis, inflammatory skin conditions, acne, rosacea, papules, pustules, telangiectasias, psoriasis, sensitive skin, redness, erythema, dermatitis, atopic dermatitis, contact dermatitis, diaper dermatitis, seborrheic dermatitis, eczema, hyperproliferative skin disease, burns, sunburn, inflammation of the vaginal mucus, vulvodynia, vaginitis, inflammation of the oral mucosa, gingivitis, periodontitis, inflammatory eye diseases, uveitis, ocular and vernal conjunctivitis, sarcoidosis, peptic ulcers, urticaria, bullous pemphigoid, scleroderma, fibrosis, angioedema, anaphylaxis, alopecia, cirrhosis of the liver, restenosis, polymyalgia rheumatica, seronegative spondyloarthropathy, including ankylosing spondylitis and Reiter's syndrome, dermatomyositis, inclusion body myositis, polymyositis and lymphangioleiomyomatosis. Preferably, the inflammation is selected from the group formed by rosacea, acne, papules, pustules, telangiectasias, sensitive skin, redness, erythema, dermatitis, eczema and psoriasis.

In another particular aspect the angiogenic disorders and/or diseases of the skin are selected, for example and not restricted to, from the group formed by psoriasis, acne, rosacea, warts, eczema, hemangiomas and lymphangiogenesis, Sturge-Weber syndrome, neurofibromatosis, tuberous sclerosis, chronic inflammatory diseases and arthritis. Preferably, the compounds of this invention are used for the treatment and/or care of rosacea.

In another particular aspect, the pigmentation disorders and/or diseases are selected, for example and not restricted to, from the group formed by freckles, lentigo, melasma, piebaldism, Addison's disease, vitiligo, spots due to exposure to UV radiation, spots due to aging, spots due to photoaging, spots caused by inflammation including due to laser treatment or post-surgery aesthetics, marks from acne, eczema, ochronosis, scars and/or hormonal disturbances including chloasmas.

In another particular embodiment, the cosmetic, non-therapeutic, treatment and/or care of the skin is a treatment, prevention, and/or care of aging and/or photoaging, treatment, prevention, and/or care of wrinkles and expression wrinkles, and/or treatment, prevention, and/or care of spots due to aging and/or photoaging. In a more particular embodiment in its treatment and/or care of the facial skin.

In another aspect, the administration of the compounds of this invention is carried out topically, transdermally, orally or parenterally. In another particular aspect the topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The compounds of the invention can be administered by any means that causes contact between the compounds and the site of action in a mammal's body, preferably that of a human being, and in the form of a composition which contains them. To this regard, the invention provides a cosmetic or pharmaceutical composition which comprises at least one compound of general formula (I), its stereoisomers, mixtures thereof, and/or its cosmetically or pharmaceutically acceptable salts. These compositions can be prepared by conventional means known to persons skilled in the art.

In another aspect, the compounds of the invention can be administered by any means that causes contact between the compounds and the site of action in a mammal's body, preferably that of a human being, and more preferably in the form of a composition which contains them. The administration of the compounds of this invention is carried out topically, transdermally, orally or parenterally. In another particular aspect the topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of application can vary greatly, depending on the needs of each subject, with a recommendation of an application range from once a month to ten times a day, preferably from once a week to four times a day, more preferably from three times a week to twice a day, even more preferably once a day.

EXAMPLES

General Methodology

All the reagents and solvents are synthesis quality and are used without any additional treatment.

Abbreviations

The abbreviations used for amino acids follow the 1983 IUPAC-IUB Commission on Biochemical Nomenclature recommendations outlined in *Eur. J. Biochem.* (1984) 138: 9-37.

®, resin; 2,6-diClZ, 2,6-dichlorobenzyl; 2-BrZ, 2-bromobenzyloxycarbonyl; 2-ClTrt-®, 2-chlorotrytyl resin; Ac, acetyl; Adpoc, 1-(1-adamantyl)-1-methylethoxy-carbonyl; Ala, alanine; All, allyl; Alloc, allyloxycarbonyl; AM, 2-[4-aminomethyl-(2,4-dimethoxyphenyl)] phenoxyacetic acid; Arg, arginine; Asn, asparagine; Boc, tert-butoxycarbonyl; Bzl, benzyl; cAMP, cyclic adenosine monophosphate; Cbz, benzyloxycarbonyl; cHx, cyclohexyl; ClZ, 2-chlorobenzyl; C-terminal, carboxy-terminal; DCM, dichloromethane; Dde, N-[1-(4,4-dimethyl-2,6-dioxocyclohex-1-iliden)ethyl; DIEA, N,N'-diisopropylethylamine; DIPCDI, N,N'-diisopropylcarbodiimide; Dmab, 4-(N-[1-(4,4-dimethyl-2,6-dioxocyclohexyliden)-3-methylbutyl]amino)benzyl; DMF, N,N-dimethylformamide; DMSO, dimethyl sulfoxide; DNA, deoxyribonucleic acid; Dnp, 2,4-dinitrophenyl; L-DOPA, L-3,4-dihydroxyphenylalanine; EDTA, ethylenediaminetetraacetic acid; equiv, equivalent; ESI-MS, electrospray ionization mass spectrometry; Fm, fluorenylmethyl; Fmoc, 9-fluorenylmethyloxycarbonyl; HDFa; human dermal fibroblasts, adult; HEPES, 4-(2-hydroxyethyl)-1-piperazine-ethanesulfonic acid; HOAt, 1-hydroxybenzotriazole; HMGS, human melanocyte growth supplement; HMGS-2, human melanocyte growth supplement without PMA (phorbol myristate acetate); HOBt, 1-hydroxybenzotriazole; HPLC, high performance liquid chromatography; IL-6, interleukin-6; IL-8, interleukin-8; INCI, International Nomenclature of Cosmetic Ingredients; ivDde, 1-(4,4-dimethyl-2,6-dioxo-cyclohexylidene)-3-methyl-butyl; KLK5, kallikrein-5; LL-37, cathelicidin C-terminal antimicrobial peptide; MBHA, p-methylbenzhydrylamine; Me, methyl; MeCN, acetonitrile; MeOH, methanol; mRNA, messenger ribonucleic acid; Mtr, 4-methoxy-2,3,6-trimethylbenzenesulfonyl; Mts, mesitylenesulfonyl; Mtt, methoxytrityl or methyltrityl; N-terminal, amino-terminal; PAL, 5-(4-aminomethyl-3,5-dimetoxyphenoxyi) valeric acid; Palm, palmitoyl; Pbf, 2,2,4,6,7-pentamethyldihydrobenzofuran-5-sulfonyl; PBS, phosphate buffered saline; PGC-1α, PPARγ coactivator 1α; Pmc, 2,2,5,7,8-pentamethylchroman-6-sulfonyl; pNZ, para-nitrobenzyloxycarbonyl; PPARγ, peroxisome proliferator-activated receptor-γ; q.s., quantity sufficient; q.s.p., quantity sufficient for; RNA, ribonucleic acid; Ser, serine; tBu, tert-butyl; Teoc, 2-(trimethylsilyl)ethyloxycarbonyl; TFA, trifluoroacetic acid; THF, tetrahydrofuran; Thr, threonine; TIS, triisopropylsilane; Tos, tosyl or p-toluenesulfonyl; Troc, 2,2,2-trichloroethyloxycarbonyl; Trt, triphenylmethyl or trityl; Val, valine; Z, benzyloxycarbonyl.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (1×1 min, 1×5 min, 5 mL/g resin) [Lloyd-Williams P. et al. (1997) *"Chemical Approaches to the Synthesis of Peptides and Proteins"* CRC, Boca Raton (FL, USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al., *"Anal. Biochem"*. (1970) 34: 595-598] or chloranil [Christensen T. *"Acta Chem. Scand"*. (1979), 33B: 763-766]. All synthetic reactions and washes were carried out at 25° C.

The HPLC chromatographic analysis was carried out with Shimadzu equipment (Kyoto, Japan) using a reversed-phase column thermostatized at 30° C. (250×4.0 mm, Kromasil $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry analysis was carried out in a WATERS Alliance ZQ 2000 detector using a mixture of MeCN:$H_2O$ 4:1 (+0.1% TFA) as the mobile phase and a flow rate of 0.3 mL/min.

Example 1 (Prophetic)

Preparation of Fmoc-$W_n$—$X_m$-$AA_1AA_2$-$AA_3$-$AA_4$-$AA_5$-$AA_6$-$Y_p$—$Z_q$—O-2-ClTrt-®, wherein $AA_1$ is a bond or -L-Ser-; $AA_2$ is -L-Ala- or -L-Val-; $AA_3$ is -L-Arg- or -L-Thr-; $AA_4$ is -L-Asn- or -L-Val-; $AA_5$ is -L-Ala- or -L-Thr-; $AA_6$ is -L-Val-; and n, m, p and q are 0.

8.8 mmol; 1 equiv of Fmoc-L-Val-OH dissolved in 55 mL of DCM, to which 0.85 equiv of DIEA is added, are incorporated into the 2-chlorotrityl dry resin (5.5 g; 8.8 mmol). They are stirred for 5 min, after which 1.64 equiv of DIEA are added. The mixture is left to react for 40 min. The remaining chloride groups are blocked by treatment with 4.4 mL of MeOH.

The N-terminal Fmoc group is deprotected as described in the general methods and 2.5 equiv of Fmoc-L-Ala-OH or Fmoc-L-Thr(tBu)-OH are coupled onto the peptidyl resin in the presence of 2.5 equiv of DIPCDI and 2.5 equiv of HOBt using DMF as a solvent for 1 hour. The resin is then washed as described in the general methods and the deprotection treatment of the Fmoc group is repeated to couple the next amino acid. Following the protocols described 2.5 equiv of Fmoc-L-Asn(Trt)-OH or Fmoc-L-Val-OH; 2.5 equiv of Fmoc-L-Arg(Pbf)-OH or Fmoc-L-Thr(tBu)-OH; 2.5 equiv of Fmoc-L-Ala-OH or Fmoc-L-Val-OH are sequentially coupled in the presence of 2.5 equiv of HOBt and 2.5 equiv of DIPCDI.

Each peptidyl-resin is divided into two halves and 2.5 equivalent of Fmoc-L-Ser(tBu)-OH are added to one in the presence of 2.5 equiv of HOBt and 2.5 equiv of DIPCDI.

After the synthesis, the peptidyl resins are washed with DCM (5×3 min) and dried by nitrogen stream.

Example 2

Obtaining Fmoc-$W_n$—$X_m$-$AA_1$-$AA_2$-$AA_3$-$AA_4$-$AA_5$-$AA_6$-$Y_p$—$Z_q$—O-2-ClTrt-®, wherein $AA_1$ is a bond; $AA_2$ is -L Ala-; AA$_3$ is -L-Thr-; AA$_4$ is -L-Asn-; AA$_5$ is -L-Thr-; AA$_6$ is a bond; and n, m, p and q are 0.

(8.8 mmol; 1 equiv) of Fmoc-L-Thr(tBu)-OH dissolved in 55 mL of DCM, to which 0.85 equiv of DIEA was added, were incorporated into the 2-chlorotrityl dry resin (5.5 g; 8.8 mmol). They were stirred for 5 min, after which 1.64 equiv of DIEA was added. It was left to react for 40 min. The remaining chloride groups were blocked by treatment with 4.4 mL of MeOH.

The N-terminal Fmoc group was deprotected as described in the general methods and 2.5 equiv of Fmoc-L-Asn-OH were coupled onto the peptidyl resin in the presence of 2.5 equiv of DIPCDI and 2.5 equiv of HOBt using DMF as a solvent for 1 hour. The resin was then washed as described in the general methods and the deprotection treatment of the Fmoc group was repeated to couple the next amino acid. Following the protocols described 2.5 equiv of Fmoc-L-Thr(tBu)-OH; 2.5 equiv of Fmoc-L-Ala-OH were sequentially coupled in the presence of 2.5 equiv of HOBt and 2.5 equiv of DIPCDI.

After the synthesis, the peptidyl resins were washed with DCM (5×3 min) and dried by nitrogen stream.

Using the same protocol, other Fmoc-W$_n$—X$_m$-AA$_1$-AA$_2$-AA$_3$-AA$_4$-AA$_5$-AA$_6$-Y$_p$—Z$_q$—O-2-ClTrt-®, wherein AA$_1$ is a bond or -L-Ser-; AA$_2$ is -L-Ala- or -L-Val-; AA$_3$ is -L-Arg- or -L-Thr-; AA$_4$ is -L-Asn- or -L-Val-; AA$_5$ is -L-Ala- or -L-Thr-; AA$_6$ is a bond; and n, m, p and q are 0, could be obtained.

Example 3

Obtaining Fmoc-W$_n$—X$_m$-AA$_1$-AA$_2$-AA$_3$-AA$_4$-AA$_5$-AA$_6$-Y$_p$—Z$_q$-AM-MBHA-®, wherein AA$_1$ is -L-Ser-; AA$_2$ is -L-Val-; AA$_3$ is -L-Arg-; AA$_4$ is -L-Val-; AA$_5$ is -L Ala-; AA$_6$ is -L-Val-; and n, m, p and q are 0.

5 mmol of the Fmoc-AM-MBHA resin with a functionalization of 0.73 mmol/g were treated with piperidine-DMF according to the described general protocol in order to remove the Fmoc group. 2.5 equiv of Fmoc-L-Val-OH were incorporated onto the deprotected resin in the presence of 2.5 equiv of DIPCDI and 2.5 equiv of HOBt using DMF as a solvent for 1 hour.

The resin was then washed as described in the general methods and the deprotection treatment of the Fmoc group was repeated to couple the next amino acid. Following the protocols described 2.5 equiv of Fmoc-L-Ala-OH; 2.5 equiv of Fmoc-L-Val-OH; 2.5 equiv of Fmoc-L-Arg(Pbf)-OH and subsequently 2.5 equiv of Fmoc-L-Val-OH were sequentially coupled in the presence of 2.5 equiv of HOBt and 2.5 equiv of DIPCDI in each coupling.

Finally, 2.5 equivalents of Fmoc-L-Ser(tBu)-OH were added in the presence of 2.5 equiv of HOBt and 2.5 equiv of DIPCDI.

After the synthesis, all the peptidyl resins were washed with DCM (5×3 min) and dried by nitrogen stream. Using the same protocol, other Fmoc-W$_n$—X$_m$-AA$_1$-AA$_2$-AA$_3$-AA$_4$-AA$_5$-AA$_6$-Y$_p$—Z$_q$-AM-MBHA-®, wherein AA$_1$ is a bond or -L-Ser-; AA$_2$ is -L-Ala- or -L-Val-; AA$_3$ is -L-Arg- or -L-Thr-; AA$_4$ is -L-Asn- or -L-Val-; AA$_5$ is -L-Ala- or -L-Thr-; AA$_6$ is -L-Val-; and n, m, p and q are 0, could be obtained.

Example 4 (Prophetic)

Preparation of Fmoc-W$_n$—X$_m$-AA$_1$-AA$_2$-AA$_3$-AA$_4$-AA$_5$-AA$_6$-Y$_p$—Z$_q$-AM-MBHA-®, wherein AA$_1$ is a bond or -L-Ser-; AA$_2$ is -L-Ala- or -L-Val-; AA$_3$ is -L-Arg- or -L-Thr-; AA$_4$ is -L-Asn- or -L-Val-; AA$_5$ is -L-Ala- or -L-Thr-; AA$_6$ is a bond; and n, m, p and q are 0.

5 mmol of the Fmoc-AM-MBHA resin with a functionalization of 0.73 mmol/g are treated with piperidine-DMF according to the described general protocol in order to remove the Fmoc group. 2.5 equiv of Fmoc-L-Ala-OH or Fmoc-L-Thr(tBu)-OH are incorporated onto the deprotected resin in the presence of 2.5 equiv of DIPCDI and 2.5 equiv of HOBt using DMF as a solvent for 1 hour.

The resin is then washed as described in the general methods and the deprotection treatment of the Fmoc group is repeated to couple the next amino acid. Following the protocols described 2.5 equiv of Fmoc-L-Asn-OH or Fmoc-L-Val-OH; 2.5 equiv of Fmoc-L-Arg(Pbf)-OH or Fmoc-L-Thr(tBu)-OH and subsequently 2.5 equiv of Fmoc-L-Ala-OH or Fmoc-L-Val-OH are sequentially coupled in the presence of 2.5 equiv of HOBt and 2.5 equiv of DIPCDI in each coupling.

Each peptidyl resin is divided into two halves and 2.5 equivalent of Fmoc-L-Ser(tBu)-OH is added to one in the presence of 2.5 equiv of HOBt and 2.5 equiv of DIPCDI.

After the synthesis, all the peptidyl resins are washed with DCM (5×3 min) and dried by nitrogen stream.

Example 5

General Process for Removal of Fmoc N-Terminal Protective Group.

The N-terminal Fmoc group of the peptidyl resins obtained in examples 2 and 3 as described in the general methods (20% piperidine in DMF, 1×1 min+1×5 min). The peptidyl resins were washed with DMF (5×1 min), DCM (4×1 min), diethyl ether (4×1 min) and dried under vacuum.

Using the same protocol the N-terminal Fmoc group of the peptidyl resins obtained in prophetic examples 1 and 4 could be deprotected, washed and dried.

Example 6 (Prophetic)

Process for Introducing the R$_1$ Palmitoyl Group onto the Peptidyl Resins Obtained in Example 5.

2.56 g of pre-dissolved palmytic acid (10 mmol; 10 equiv) pre-dissolved in DMF (1 mL) are incorporated onto 1 mmol of the peptidyl resins in Example 5, in the presence of 1.53 g of HOBt (10 mmol; 10 equiv) and 1.56 mL of DIPCDI (10 mmol; 10 equiv). They are allowed to react for 15 hours, after which the resins are washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and are dried under vacuum.

Example 7

Process for Introducing the R$_1$ Acetyl Group onto the Peptidyl Resins Obtained in Example 5.

1 mmol of the peptidyl resins obtained in Example 5 was treated with 25 equiv of acetic anhydride in the presence of 25 equiv of DIEA using 5 mL of DMF as a solvent. They were left to react for 30 mins, after which the peptidyl resins were washed with DMF (5×1 min), DCM (4×1 min), diethyl ether (4×1 min) and were dried under vacuum.

Following the same protocol, the R$_1$ acetyl group could be introduced onto the peptidyl resins obtained in prophetic Example 5.

Example 8

Cleavage Process from the Polymeric Support of the Peptidyl Resins Obtained in Example 7.

200 mg of the dried peptidyl resins obtained in Example 7 were treated with 5 mL of TFA:TIS:H$_2$O (90:5:5) for 2 hours at room temperature under stirring. The filtrates were collected onto 50 mL cold diethyl ether, they were filtered through polypropylene syringes fitted with porous polyethylene discs and washed 5 times with 50 mL diethyl ether. The final precipitates were dried under vacuum.

HPLC analysis of the obtained peptides in gradients of MeCN (+0.07% TFA) in $H_2O$ (+0.1% TFA) showed a purity exceeding 80% in all cases. The identity of the peptides obtained was confirmed by ESI-MS.

Prophetically, following the same protocol the cleavage from the polymeric support is performed for the other peptidyl resins prophetically obtained in Examples 5 to 7.

Example 9 (Prophetic)

Cleavage Process of the Polymeric Support and Functionalization with $R_2$ Substituted Amine: Obtaining Ac—$W_n$—$X_m$-$AA_1$-$AA_2$-$AA_3$-$AA_4$-$AA_5$-$AA_6$-$Y_p$—$Z_q$—NH—$(CH_2)_{15}$—$CH_3$, wherein $AA_1$ is a bond or -L-Ser-; $AA_2$ is -L-Ala- or -L-Val-; $AA_3$ is -L-Arg- or -L-Thr-; $AA_4$ is -L-Asn- or -L-Val-; $AA_5$ is -L-Ala- or -L-Thr-; $AA_6$ is a bond or -L-Val-; and n, m, p and q are 0.

The peptides Ac—$W_n$—$X_m$-$AA_1$-$AA_2$-$AA_3$-$AA_4$-$AA_5$-$AA_6$-$Y_p$—$Z_q$—OH with fully protected side chains were obtained or are prophetically obtained by treating 150 mg of the peptidyl resins Ac—$W_n$—$X_m$-$AA_1$-$AA_2$-$AA_3$-$AA_4$-$AA_5$-$AA_6$-$Y_p$—$Z_q$—O-2-ClTrt-® of Example 7, previously desiccated under vacuum in the presence of KOH, with 3 mL of a 3% solution of TFA in DCM for 5 min. The filtrates were collected onto 50 mL of cold diethyl ether and the treatment was repeated three times. The ethereal solutions are evaporated to dryness at reduced pressure and room temperature, the precipitates are redissolved in 50% MeCN in $H_2O$ and lyophilized. 10 mg of the obtained crude peptides are weighed in a flask and 3 equiv of hexadecylamine and 25 mL of anhydrous DMF are added. 2 equiv of DIPCDI are added, and left to react under magnetic stirring at 47° C. The reactions are monitored by HPLC until disappearance of the initial products, which are complete after 24-48 hours. The solvents are evaporated to dryness and co-evaporated twice with DCM. The obtained residues [Ac—$W_n$—$X_m$-$AA_1$-$AA_2$-$AA_3$-$AA_4$-$AA_5$-$AA_6$-$Y_p$—$Z_q$—NH—$(CH_2)_{15}$—$CH_3$ with fully protected side chains] are redissolved in 25 mL of a mixture of TFA:DCM:anisol (49:49:2) and left to react for 30 min at room temperature. 250 mL of cold diethyl ether are added, the solvents are evaporated under reduced pressure and two additional co-evaporations with ether are carried out. The residues are dissolved in a mixture of 50% MeCN in $H_2O$ and lyophilized.

Example 10

Evaluation of the Inhibitory Capacity of Compounds on the Pro-Inflammatory Activity of the Antimicrobial Peptide LL-37 in Primary Keratinocytes Solutions of the compounds of the invention were prepared in Eppendorf tubes at the desired concentrations in complete Epilife® medium with and without LL-37 at 50 μg/mL in a final volume of 250 μL. The mixtures were incubated in rotation for 1 hour at room temperature. After the preincubation hour the samples were collected and they were given a quick pulse in the centrifuge to push all the solution to the bottom of the tube. Without removing the incubation medium, it was added to the 50 μL/well cells of the previous mixtures in quadruplicate and the plate was incubated at 37° C. in a $CO_2$ incubator for 1 hour. After the hour of incubation, 50 μL/well of complete Epilife® medium were added. They were incubated for another 5 hours to allow the release of pro-inflammatory cytokines induced by LL-37 for their subsequent quantification by ELISA. After the 5 hours, the 300 μL of supernatants were collected with the multi-channel pipette and passed to a new 96-well plate and the quantity of IL-6 and IL-8 released was determined by the Human IL-6 ELISA Ready-SET-GO!® and Human IL-8 ELISA Ready-SET-GO!® commercial kits (eBioscience, Inc.) following the supplier's instructions. The absorbency of each well was determined by reading a Multiskan Ascent Reader spectrophotometer at 450 nm correcting for each determination with its corresponding reading at 570 nm. The standardized relative levels of IL-6 and IL-8 were calculated with regard to the absorbency corresponding to the treatment of the cells with carrier. Next, the total number of cells per well was quantified with Cristal Violeta, in order to be able to calculate the percentage of interleukins released per cell.

Table 3 details the peptides that showed values of inhibition of the release of IL-6 induced by LL-37 in primary keratinocytes in the tested conditions, representing the results as % of IL-6. In table 4 the results obtained from the release of IL-8 are detailed.

TABLE 3

Inhibition of the release of IL-6 induced by LL-37 in primary human keratinocytes

| Treatment | % IL-6 |
|---|---|
| Carrier | 100% |
| Positive control (LL-37 0.05 mg/ml) | 122.28% |
| 0.025 mg/mL Ac-L-Ala-L-Thr-L-Asn-L-Thr-OH (Ac-(SEQ ID NO: 16)-OH) | 107.25% |
| 0.025 mg/mL Ac-L-Ser-L-Val-L-Arg-L-Val-L-Ala-L-Val-$NH_2$ (Ac-(SEQ ID NO: 2)-$NH_2$) + LL-37 0.05 mg/ml | 108.35% |
| 0.1 mg/mL Ac-L-Ala-L-Thr-L-Asn-L-Thr-OH (Ac-(SEQ ID NO: 16)-OH) + LL-37 0.05 mg/ml | 94.65% |
| 0.1 mg/mL Ac-L-Ser-L-Val-L-Arg-L-Val-L-Ala-L-Val-$NH_2$ (Ac-(SEQ ID NO: 2)-$NH_2$) + LL-37 0.05 mg/ml | 95.96% |
| 0.5 mg/mL Ac-L-Ala-L-Thr-L-Asn-L-Thr-OH (Ac-(SEQ ID NO: 16)-OH) + LL-37 0.05 mg/ml | 92.90% |
| 0.5 mg/mL Ac-L-Ser-L-Val-L-Arg-L-Val-L-Ala-L-Val-$NH_2$ (Ac-(SEQ ID NO: 2)-$NH_2$) + LL-37 0.05 mg/ml | 93.15% |

TABLE 4

Inhibition of the release of IL-8 induced by LL-37 in primary human keratinocytes

| Treatment | % IL-8 |
|---|---|
| Carrier | 100% |
| Positive control (LL37 0.05 mg/ml) | 142.65% |
| 0.025 mg/mL Ac-L-Ala-L-Thr-L-Asn-L-Thr-OH (Ac-(SEQ ID NO: 16)-OH) + LL-37 0.05 mg/ml | 132.70% |
| 0.025 mg/mL Ac-L-Ser-L-Val-L-Arg-L-Val-L-Ala-L-Val-$NH_2$ (Ac-(SEQ ID NO: 2)-$NH_2$) + LL-37 0.05 mg/ml | 132.92% |

TABLE 4-continued

Inhibition of the release of IL-8 induced by LL-37 in primary human keratinocytes

| Treatment | % IL-8 |
|---|---|
| 0.1 mg/mL Ac-L-Ala-L-Thr-L-Asn-L-Thr-OH (Ac-(SEQ ID NO: 16)-OH) + LL-37 0.05 mg/ml | 124.76% |
| 0.1 mg/mL Ac-L-Ser-L-Val-L-Arg-L-Val-L-Ala-L-Val-NH$_2$ (Ac-(SEQ ID NO: 2)-NH$_2$) + LL-37 0.05 mg/ml | 125.05% |
| 0.5 mg/mL Ac-L-Ala-L-Thr-L-Asn-L-Thr-OH (Ac-(SEQ ID NO: 16)-OH) + LL-37 0.05 mg/ml | 109.39% |
| 0.5 mg/mL Ac-L-Ser-L-Val-L-Arg-L-Val-L-Ala-L-Val-NH$_2$ (Ac-(SEQ ID NO: 2)-NH$_2$) + LL-37 0.05 mg/ml | 109.24% |

Example 11

Preparation of a Water in Oil (w/o) Emulsion Containing Ac-L-Ala-L-Thr-L-Asn-L-Thr-OH (Ac-(SEQ ID NO: 16)-OH).

In a suitable vessel soybean oil [INCI: SOYBEAN (*GLYCINE SOJA*) OIL], Abil EM 90 [INCI: CETYL PEG/PPG-10/1 DIMETHICONE] and SPAN 65 [INCI: SORBITAN TRISTEARATE] were mixed together. In a separate vessel, the peptide Ac-L-Ala-L-Thr-L-Asn-L-Thr-OH (Ac-(SEQ ID NO: 16)-OH) and water [INCI: WATER (AQUA)] were mixed together. Both the aqueous and oleous phases were heated to 75-80° C., after which the aqueous phase was added to the oleous phases little by little under stirring. Once the emulsion had been formed, the particle size was reduced using ultrasound, obtaining a cosmetic composition with the proportions shown in Table 5.

TABLE 5

Emulsion W/O containing Ac-L-Ala-L-Thr-L-Asn-L-Thr-OH (Ac-(SEQ ID NO: 16)-OH)

| Phase | Ingredients | % in peso |
|---|---|---|
| A | WATER (AQUA) | 53 |
| B | SOYBEAN (*GLYCINE SOJA*) OIL | 33 |
| B | CETYL PEG/PPG-10/1 DIMETHICONE | 5 |
| B | SORBITAN TRISTEARATE | 4 |
| A | Ac-L-Ala-L-Thr-L-Asn-L-Thr-OH | 5 |

Example 12

Preparation of Coacervates of Nanostructured Lipid Carriers Containing Ac-L-Ala-L-Thr-L-Asn-L-Thr-OH (Ac-(SEQ ID NO: 16)-OH).

PHASE A: In a suitable vessel the following were added in this order: water [INCI: WATER (AQUA)], Zemea [INCI: PROPANEDIOL], Phenoxyethanol [INCI: PHENOXYETHANOL], Structure® XL [INCI: HYDROXYPROPYL STARCH PHOSPHATE], Amigel [INCI: *SCLEROTIUM* GUM] and hyaluronic acid [INCI: HYALURONIC ACID]. The mixture was heated to 60-65° C.

PHASE B: In another vessel Massocare HD [INCI: ISOHEXADECANE], Arlacel™ 83 Pharma [INCI: SORBITAN SESQUIOLEATE], Lipochroman™ [INCI: DIMETHYLMETHOXY CHROMANOL] and the W/O emulsion described in Example 11 (PHASE B1) were added and heated to 60-65° C.

PHASE C: The following ingredients were mixed together in a suitable vessel: Water [INCI: WATER (AQUA)], Structure® XL [INCI: HYDROXYPROPYL STARCH PHOSPHATE], Amigel [INCI: *SCLEROTIUM* GUM], Sepigel™ 305 [INCI: POLYACRYLAMIDE, WATER (AQUA), C13-14 ISOPARAFFIN, LAURETH-7] and Quad Soy LDMA [INCI: WATER (AQUA), LAURYLDIMONIUM HYDROXYPROPYL HYDROLYZED SOY PROTEIN].

Phase B was added to phase A little by little under stirring until an emulsion was formed, after which the mixture was microfluidified. Phase C was added under constant stirring, obtaining a cosmetic composition with the proportions shown in Table 6.

TABLE 6

Coacervates of nanostructured lipid carriers

| Phase | Ingredients | % weight |
|---|---|---|
| C | WATER (AQUA) | 19.79 |
| C | HYDROXYPROPYL STARCH PHOSPHATE | 1.5 |
| C | SCLEROTIUM GUM | 0.75 |
|  | Sepigel ™ 305 (POLYACRYLAMIDE, |  |
| C | WATER (AQUA), C13-14 ISOPARAFFIN, LAURETH-7) |  |
|  | POLYACRYLAMIDE | 0.1 |
|  | WATER (AQUA) | 0.0863 |
|  | C13-14 ISOPARAFFIN | 0.05 |
|  | LAURETH-7 | 0.0137 |
|  | Quad Soy LDMA (WATER (AQUA), |  |
| C | LAURYLDIMONIUM HYDROXYPROPYL HYDROLYZED SOY PROTEIN) |  |
|  | WATER (AQUA) | 0.14 |
|  | LAURYLDIMONIUM HYDROXYPROPYL HYDROLYZED SOY PROTEIN | 0.06 |
| A | WATER (AQUA) | 50.30 |
| B | ISOHEXADECANE | 5.03 |
| A | PROPANEDIOL | 5.03 |
| B | SORBITAN SESQUIOLEATE | 4.02 |
| A | PHENOXYETHANOL | 2.62 |
| A | HYDROXYPROPYL STARCH PHOSPHATE | 0.3 |
| A | SCLEROTIUM GUM | 0.1 |
| B | DIMETHYLMETHOXY CHROMANOL | 0.05 |
| A | HYALURONIC ACID | 0.01 |
| B1 | WATER (AQUA) | 5.33 |
| B1 | SOYBEAN (*GLYCINE SOJA*) OIL | 3.32 |
| B1 | CETYL PEG/PPG-10/1 DIMETHICONE | 0.5 |
| B1 | Ac-L-Ala-L-Thr-L-Asn-L-Thr-OH Ac-(SEQ ID NO: 16)-OH) | 0.5 |
| B1 | SORBITAN TRISTEARATE | 0.4 |

Example 13

Preparation of Liposomes Containing Ac-L-Ala-L-Thr-L-Asn-L-Thr-OH (Ac-(SEQ ID NO: 16)-OH).

In a suitable vessel the following components were dissolved: water [INCI: WATER (AQUA)], Zemea Propanediol [INCI: PROPANEDIOL], phenoxyethanol [INCI: PHENOXYETHANOL] and the peptide Palm-L-Ala-L-Thr-L-Asn-L-Thr-NH$_2$ (Palm-(SEQ ID NO: 16)-NH$_2$). Once all the components had been dissolved, lecithin [INCI: LECITHIN] was slowly added under stirring. Once the multilamellar liposomes had been formed they were microfluidified to reduce the particle size until small liposomes were obtained. In table 7 the components which form the liposomes are shown.

TABLE 7

Liposomes containing Ac-L-Ala-L-Thr-L-Asn-L-Thr-OH (Ac-(SEQ ID NO: 16)-OH)

| Phase | Ingredients | % weight |
|---|---|---|
| A | WATER (AQUA) | 88.25 |
| A | PROPANEDIOL | 5.0 |
| A | PHENOXYETHANOL | 2.5 |
| A | Ac-L-Ala-L-Thr-L-Asn-L-Thr-OH (Ac-(SEQ ID NO: 16)-OH) | 0.25 |
| B | LECITHIN | 4.0 |

Example 14

Preparation of a Cosmetic Facial Composition Containing Ac-L-Ala-L-Thr-L-Asn-L-Thr-OH (Ac-(SEQ ID NO: 16)-OH).

The components from PHASE A: Water [INCI: WATER (AQUA)], Liponic® EG-1 [INCI: GLYCERETH-26], Hydrolite®-5 2/016020 [INCI: PENTYLENE GLYCOL], Microcare® BNA [INCI: BENZYL ALCOHOL], glycerin [INCI: GLYCERIN] were incorporated in a suitable vessel. Once they had all been incorporated, Carbopol Ultrez® 10 [INCI: CARBOMER] was added little by little under stirring. The mixture was heated to 70-75° C.

In a separate vessel, PHASE B was prepared: Massocare™ TH [INCI: TRIETHYLHEXANOIN], Finsolv®-TN [INCI: C12-15 ALKYL BENZOATE], Arlacel™ 165 [INCI: GLYCERYL STEARATE, PEG-100 STEARATE], phenoxyethanol [INCI: PHENOXYETHANOL], cetyl alcohol [INCI: CETYL ALCOHOL] and stearyl alcohol [INCI: STEARYL ALCOHOL]. The whole mixture was heated to 70-75° C.

Once PHASES A and B had been prepared, the heated phase B was added to PHASE A, little by little under constant stirring with a turbine to form an O/W emulsion. When the temperature dropped from 50° C. and maintaining stirring with a turbine, PHASE C: Trylagen® PCB [INCI: WATER (AQUA), PSEUDOALTEROMONAS FERMENT EXTRACT, HYDROLYZED WHEAT PROTEIN, HYDROLYZED SOY PROTEIN, TRIPEPTIDE-10 CITRULLINE, TRIPEPTIDE-1, LECITHIN, BUTYLENE GLYCOL, XANTHAN GUM, CARBOMER, TRIETHANOLAMINE, CAPRYLYL GLYCOL, PHENOXYETHANOL], Silicon DC 345 Fluid [INCI: CYCLOMETHICONE] and the peptide Ac-L-Ala-L-Thr-L-Asn-L-Thr-OH (Ac-(SEQ ID NO: 16)-OH) previously dissolved in water and butylene glycol [INCI: BUTYLENE GLYCOL] was added. Once the emulsion had reached room temperature, the pH was adjusted to 6.0-6.5 with sodium hydroxide [INCI: SODIUM HYDROXIDE] and the fragrance was added [INCI: FRAGRANCE (PARFUM)]. In table 8 the ingredients that form the formula are shown:

TABLE 8

Cosmetic facial composition containing Ac-L-Ala-L-Thr-L-Asn-L-Thr-OH (Ac-(SEQ ID NO: 16)-OH)

| Phase | Ingredients | % weight |
|---|---|---|
| A | WATER (AQUA) | qsp 100 |
| A | GLYCERETH-26 | 5.0 |
| A | PENTYLENE GLYCOL | 5.0 |
| C | TRYLAGEN ® PCB (WATER (AQUA), PSEUDOALTEROMONAS FERMENT EXTRACT, HYDROLYZED WHEAT PROTEIN, HYDROLYZED SOY PROTEIN, TRIPEPTIDE-10 CITRULLINE, TRIPEPTIDE-1, LECITHIN, BUTYLENE GLYCOL, XANTHAN GUM, CARBOMER, TRIETHANOLAMINE, CAPRYLYL GLYCOL, PHENOXYETHANOL) | |
| | WATER (AQUA) | 2.40 |
| | PSEUDOALTEROMONAS FERMENT EXTRACT | 0.372 |
| | HYDROLYZED WHEAT PROTEIN | 0.086 |
| | HYDROLYZED SOY PROTEIN | 0.056 |
| | TRIPEPTIDE-10 CITRULLINE | 0.001 |
| | TRIPEPTIDE-1, | 0.0003 |
| | LECITHIN | 0.012 |
| | BUTYLENE GLYCOL | 0.017 |
| | XANTHAN GUM | 0.013 |
| | CARBOMER | 0.0008 |
| | TRIETHANOLAMINE | 0.0001 |
| | CAPRYLYL GLYCOL | 0.017 |
| C | CYCLOMETHICONE | 3.0 |
| B | TRIETHYLHEMNOIN | 3.0 |
| B | C12-15 ALKYL BENZOATE | 3.0 |
| B | Ac-L-Ala-L-Thr-L-Asn-L-Thr-OH (Ac-(SEQ ID NO: 16)-OH) | 0.001 |
| B | WATER (AQUA) | 0.9995 |
| B | BUTYLENE GLYCOL | 0.9995 |
| B | ARLACEL ™ 165 (GLYCERYL STEARATE, PEG-100 STEARATE) | |
| | GLYCERYL STEARATE | 0.75 |
| | PEG-100 STEARATE | 0.75 |
| A | BENZYL ALCOHOL | 1.0 |
| A | GLYCERIN | 1.0 |
| B | PHENOXYETHANOL | 0.9 |
| A | CARBOMER | 0.5 |
| B | CETYL ALCOHOL | 0.5 |
| B | STEARYL ALCOHOL | 0.5 |
| E | FRAGRANCE (PARFUM) | 0.15 |
| D | SODIUM HYDROXIDE | qsp pH 6-6.5 |

Example 15 (Prophetic)

Preparation of a Facial Serum Containing Ac-L-Ser-L-Val-L-Arg-L-Val-L-Ala-L-Val-OH (Ac-(SEQ ID NO: 2)-NH$_2$).

In a suitable vessel the components from PHASE A: Water [INCI: WATER (AQUA)], Liponic® EG-1 [INCI: GLYCERETH-26], Hydrolite®-5 2/016020 [INCI: PENTYLENE GLYCOL], Microcare® BNA [INCI: BENZYL ALCOHOL], glycerin [INCI: GLYCERIN] and propylene glycol [INCI: PROPYLENE GLYCOL] are added. Next, Carbopol® Ultrez 10 [INCI: CARBOMER] is added slowly under stirring.

In a separate vessel, PHASE B: Massocare TH [INCI: TRIETHYLHEXANOIN], phenoxyethanol [INCI: PHENOXYETHANOL] is prepared and added little by little under stirring to phase A.

Once phases A and B have been mixed together, the following components are added one by one under stirring: Preventhelia® solution [INCI: WATER (AQUA), DIAMINOPROPIONOYL TRIPEPTIDE-33, CAPRYLYL GLYCOL], Silicon DC 200 [INCI: DIMETHICONE], silicon DC 245 [INCI: CYCLOPENTASILOXANE], Sepigel™ 305 [INCI: POLYACRYLAMIDE, WATER (AQUA), C13-14 ISOPARAFFIN,LAURETH-7] and the peptide Ac-L-Ser-L-Val-L-Arg-L-Val-L-Ala-L-Val-OH (Ac-(SEQ ID NO: 2)-NH$_2$) previously dissolved in water and butylene glycol [INCI: BUTYLENE GLYCOL].

In a separate vessel the fragrance [INCI: FRAGRANCE (PARFUM)] is mixed with Cremophor® CO 40 [INCI: PEG-40 HYDROGENATED CASTOR OIL] and added to the previous mixture. Finally, the pH is adjusted to 6.0-6.5 with sodium hydroxide [INCI: SODIUM HYDROXIDE].

In table 9 the ingredients that form the formula are shown:

TABLE 9

Facial serum containing Ac-L-Ser-L-Val-L-Arg-L-Val-L-Ala-L-Val-OH

| Phase | Ingredients | % weight |
|---|---|---|
| A | WATER (AQUA) | qsp 100 |
| A | GLYCERETH-26 | 5.0 |
| A | PENTYLENE GLYCOL | 5.0 |
| A | BENZYL ALCOHOL | 1.0 |
| A | GLYCERIN | 2.0 |
| A | PROPYLENE GLYCOL | 3.0 |
| A | CARBOMER | 0.3 |
| C | Ac-L-Ser-L-Val-L-Arg-L-Val-L-Ala-L-Val-OH (Ac-(SEQ ID NO: 2)-NH$_2$) | 0.001 |
| C | WATER (AQUA) | 0.9995 |
| C | BUTYLENE GLYCOL | 0.9995 |
| B | TRIETHYLHEXANOIN | 2.0 |
| B | PHENOXYETHANOL | 0.9 |
| C | PREVENTHELIA ® SOLUTION (WATER (AQUA), DIAMINOPROPIONOYL TRIPEPTIDE-33, CAPRYLYL GLYCOL ) | |
| | WATER (AQUA) | 1.989 |
| | DIAMINOPROPIONOYL TRIPEPTIDE-33 | 0.001 |
| | CAPRYLYL GLYCOL | 0.01 |
| C | DIMETHICONE | 0.5 |
| C | CYCLOPENTASILOXANE | 0.5 |
| C | SEPIGEL ™ 305 (POLYACRYLAMIDE, WATER (AQUA), C13-14 ISOPARAFFIN, LAURETH-7) | |
| | POLYACRYLAMIDE | 0.04 |
| | WATER (AQUA) | 0.0345 |
| | C13-14 ISOPARAFFIN | 0.02 |
| | LAURETH-7 | 0.0055 |
| D | PEG-40 HYDROGENATED CASTOR OIL | 0.6 |
| D | FRAGRANCE (PARFUM) | 0.15 |
| E | SODIUM HYDROXIDE | qsp pH 6-6.5 |

Example 16

Preparation of a Facial Cosmetic Composition Containing Ac-L-Ala-L-Thr-L-Asn-L-Thr-OH (Ac-(SEQ ID NO: 16)-OH).

In a suitable vessel the components of PHASE A: Water [INCI: WATER (AQUA)], Hydrolite®-5 2/016020 [INCI: PENTYLENE GLYCOL] and Microcare® BNA [INCI: BENZYL ALCOHOL] were incorporated. Next, Carbopol® Ultrez 10 [INCI: CARBOMER] was added little by little under stirring. The mixture was heated to 65-70° C.

In another vessel the components of PHASE B: Massocare™ EC [INCI: ETHYLHEXYL COCOATE], Finsolv® TN [INCI: C12-15 ALKYL BENZOATE], phenoxyethanol [INCI: PHENOXYETHANOL], Arlatone™ MAP 160 K [INCI: POTASSIUM CETYL PHOSPHATE] and Phytocream® 2000 [INCI: GLYCERYL STEARATE, CETEARYL ALCOHOL, POTASSIUM PALMITOYL HYDROLYZED WHEAT PROTEIN] were incorporated, and the mixture was heated to 65-70° C.

Phase B was added to phase A slowly under stirring with a turbine. When the temperature reached 40° C., the following components were added one by one: Silicon DC 200 [INCI: DIMETHICONE], Vitamin E acetate [INCI: TOCOPHERYL ACETATE], Sepigel™ 305 [INCI: POLYACRYLAMIDE, WATER (AQUA), C13-14 ISOPARAFFIN, LAURETH-7] and the peptide Ac-L-Ala-L-Thr-L-Asn-L-Thr-OH (Ac-(SEQ ID NO: 16)-OH) previously dissolved in water and butylene glycol [INCI: BUTYLENE GLYCOL]. Lastly, the fragrance was added [INCI: FRAGRANCE (PARFUM)] and the pH was adjusted to 6.0-6.5 with sodium hydroxide [INCI: SODIUM HYDROXIDE]. In table 10 the % of the ingredients used in this formulation are shown.

TABLE 10

Facial cosmetic composition containing Ac-L-Ala-L-Thr-L-Asn-L-Thr-OH (Ac-(SEQ ID NO: 16)-OH)

| Phase | Ingredients | % weight |
|---|---|---|
| A | WATER (AQUA) | qsp 100 |
| A | PENTYLENE GLYCOL | 5.0 |
| A | BENZYL ALCOHOL | 1.0 |
| A | CARBOMER | 0.5 |
| B | ETHYLHEXYL COCOATE | 2.5 |
| B | C12-15 ALKYL BENZOATE | 5.0 |
| B | PHENOXYETHANOL | 0.9 |
| B | POTASSIUM CETYL PHOSPHATE | 0.5 |
| B | PHYTOCREAM ® 2000 (GLYCERYL STEARATE, CETEARYL ALCOHOL, POTASSIUM PALMITOYL HYDROLYZED WHEAT PROTEIN) | |
| | GLYCERYL STEARATE | 1.0 |
| | CETEARYL ALCOHOL | 2.0 |
| | POTASSIUM PALMITOYL HYDROLYZED WHEAT PROTEIN | 2.0 |
| C | DIMETHICONE | 1.0 |
| C | TOCOPHERYL ACETATE | 0.5 |
| C | SEPIGEL ™ 305 | 1.0 |
| C | Ac-L-Ala-L-Thr-L-Asn-L-Thr-OH (Ac-(SEQ ID NO: 16)-OH) | 0.001 |
| C | WATER (AQUA) | 0.9995 |
| C | BUTYLENE GLYCOL | 0.9995 |
| D | FRAGRANCE (PARFUM) | 0.1 |
| E | SODIUM HYDROXIDE | qsp pH 6-6.5 |

Example 17

Effect of the Composition of Example 16 on the Treatment of Skin with Slight Rosacea.

An evaluation study of the improvement of skin with a tendency to suffer from rosacea was carried out. Twenty volunteers over the age of 18 participated in the study, both men and women, with healthy skin but with slight rosacea without the need for medical treatment. All the volunteers were assessed by a dermatologist to verify that they met the requirements necessary to take part in the trial. Exclusion factors took into account whether the volunteers suffered any type of inflammation or disease (one-off or chronic), as well as whether they took any kind of medication that could alter the results. During the trial the volunteers could not expose themselves to ultraviolet radiation or apply any kind of cosmetic product (up to 7-10 days before the start of the test). Furthermore, volunteers who had had any kind of allergy or secondary effects to any cosmetic products, people with cancer and pregnant women were excluded.

The volunteers applied the product described in example 16 to their faces twice a day for 4 weeks. A dermatological assessment was undertaken before the treatment and after 1 and 4 weeks of application of the product. The parameters assessed were erythema, redness of the face, spread of rosacea on the skin and roughness of the skin. The assessment of the parameters was carried out by numerical allocation with a scale of 0 to 100, 0 being the value corresponding to "NO INTENSITY" and 100 to "MAXIMUM INTENSITY".

An instrumental assessment was also carried out on the redness of the skin using the VISIA™ system in which the red spots found on the area of skin studied were assessed, and an absolute value was allocated to the intensity and area of the red spots. This assessment was carried out at 0 weeks and after 4 weeks of the treatment.

The results of the activity of the cream of example 16 on skin with rosacea are shown in table 11.

TABLE 11

Activity of a cosmetic facial composition containing Ac-L-Ala-L-Thr-L-Asn-L-Thr-OH (Ac-(SEQ ID NO: 16)-OH) on skin with rosacea.

| Parameter | $T_{1\ week}$-$T_0$ | $T_{4\ weeks}$-$T_0$ |
|---|---|---|
| Erythema | −9.0% | −19.2% |
| Redness of the skin | −8.6% | −17.7% |
| Spread of the rosacea | −7.9% | −17.9% |
| Roughness | −5.4% | −7.5% |
| Absolute value of the redness (VISIA ™) | — | −14.4% |
| Red spots (VISIA ™) | — | −8.3% |

Example 18

Anti-Collagenase Activity of the Peptide Ac-L-Ala-L-Thr-L-Asn-L-Thr-OH (Ac-(SEQ ID NO: 16)-OH).

Different concentrations of the peptide Ac-L-Ala-L-Thr-L-Asn-L-Thr-OH (Ac-(SEQ ID NO: 16)-OH) were incubated in a 96-well plate together with fluorescein-derivatized gelatin, a fluorescent marker. Next, collagenase (0.4 U/mL) was added and incubated at room temperature protected from sunlight for 2 hours, after which the fluorescence ($\lambda_{exc}$=495 nm and $\lambda_{em}$=515 nm) was measured at different points, thus the breakage in the derivatized gelatin could be quantified. As a positive control 1,10-phenanthroline was used, a metal chelator which acts as an inhibitor of metalloproteases. The results obtained are shown in table 12.

TABLE 12

Modulation of the activity of the anti-collagenase enzyme by the peptide Ac-L-Ala-L-Thr-L-Asn-L-Thr-OH (Ac-(SEQ ID NO: 16)-OH).

| Treatment | % collagenase inhibition |
|---|---|
| Carrier (buffer reaction) | 0% |
| Positive control (1,10-phenanthroline 40 μg/mL) | 95.19% |
| 10 mg/mL Ac-L-Ala-L-Thr-L-Asn-L-Thr-OH | 100% |
| 2 mg/mL Ac-L-Ala-L-Thr-L-Asn-L-Thr-OH | 29.21% |

Example 19

Anti-Tyrosinase Activity of the Peptide Ac-L-Ala-L-Thr-L-Asn-L-Thr-OH (Ac-(SEQ ID NO: 16)-OH).

Different concentrations of the peptide Ac-L-Ala-L-Thr-L-Asn-L-Thr-OH (Ac-(SEQ ID NO: 16)-OH) were incubated in a 96-well plate together with L-DOPA in a HEPES buffer for 30 minutes at 37° C. After incubation, the tyrosinase enzyme was added and incubated for 10 minutes. The reaction was stopped freezing the plate at −20° C. for 5 minutes, after which the absorbency was measured at $\lambda_{exc}$=490 nm in a microplate reader. As a positive control kojic acid was added, a substance with known anti-tyrosinase activity. The results obtained are shown in table 13.

TABLE 13

Modulation of the activity of the anti-tyrosinase enzyme by the peptide Ac-L-Ala-L-Thr-L-Asn-L-Thr-OH (Ac-(SEQ ID NO: 16)-OH).

| Treatment | % tyrosinase inhibition |
|---|---|
| Carrier (buffer reaction) | 0% |
| Positive control (kojic acid 140 μg/mL) | 85.79% |
| 4 mg/mL Ac-L-Ala-L-Thr-L-Asn-L-Thr-OH | 86.45% |
| 3 mg/mL Ac-L-Ala-L-Thr-L-Asn-L-Thr-OH | 76.01% |
| 2 mg/mL Ac-L-Ala-L-Thr-L-Asn-L-Thr-OH | 38.23% |

Example 20

Inhibition of melanogenesis in human epidermal melanocytes by the peptide Ac-L-Ala-L-Thr-L-Asn-L-Thr-OH (Ac-(SEQ ID NO: 16)-0H).

Primary human melanocytes were cultivated in medium 254 supplemented by HMGS and antibiotics. The cells were grown for 72 hours after which the medium was changed to 254 supplemented by HMGS-2 and antibiotics. The cells were grown until confluence for 2 weeks, changing the medium every 2-3 days. After two weeks, the cells were trypsinized and seeded in 6-well plates. After being incubated for a whole night at 37° C. and 5% of $CO_2$, the first treatment with the peptide was carried out at different concentrations. As a negative control, only medium was added. The treatment was repeated on days 3, 6, 8 and 10, after which the cells were trypsinized and the number counted with a cell counter. Melanin was quantified by measuring the absorbency at 450 nm with a microplate reader and the value was standardized with regard to the total number of cells per well, expressed as picograms of melanin per cell from a calibration line prepared with synthetic melanin dissolved in 1 N NaOH with 10% DMSO. The results obtained and standardized with regard to the control are shown in table 14.

TABLE 14

Inhibition of melanogenesis in human epidermal melanocytes by the peptide Ac-L-Ala-L-Thr-L-Asn-L-Thr-OH (Ac-(SEQ ID NO: 16)-OH).

| Treatment | % melanin (pg/cel) |
|---|---|
| Control (culture medium) | 100 ± 0.6 |
| 0.25 mg/mL Ac-L-Ala-L-Thr-L-Asn-L-Thr-OH | 45.7 ± 3.2 |
| 0.625 mg/mL Ac-L-Ala-L-Thr-L-Asn-L-Thr-OH | 55.8 ± 2.8 |

Example 21

Photoprotection of Human Fibroblasts by the Peptide Ac-L-Ala-L-Thr-L-Asn-L-Thr-OH (Ac-(SEQ ID NO: 16)-OH).

The photoprotection of human fibroblasts is based on the determination of the protective effect of a substance in the presence of a simulated cytotoxic dose of sunlight. To study this effect, human fibroblasts HDFa were cultivated for 24 hours in 96-well plates, after which they were incubated with different concentrations of the peptide Ac-L-Ala-L-Thr-L-Asn-L-Thr-OH (Ac-(SEQ ID NO: 16)-OH) or buffer PBS (CRT+UV) in the case of the control for 1 hour in darkness at 37° C., 5% $CO_2$ and humidified air. Next, the cells were exposed to room temperature at a radiation dose of 36 J/cm². As a control, a plate was kept in the dark for the same time (CRT-UV), and then the viability was determined with the neutral red method. The results are shown in table 15:

TABLE 15

Photoprotection of human fibroblasts by the
peptide Ac-L-Ala-L-Thr-L-Asn-L-Thr-OH (Ac-(SEQ ID NO: 16)-OH).

| Treatment | % cell viability |
|---|---|
| CRT − UV | 100 ± 0.85 |
| CRT + UV | 20.03 ± 2.24 |
| 10 mg/mL Ac-L-Ala-L-Thr-L-Asn-L-Thr-OH | 63.25 ± 1.30 |
| 1 mg/mL Ac-L-Ala-L-Thr-L-Asn-L-Thr-OH | 52.37 ± 4.775 |

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The Sequence listing entitled LPTC 200029.txt filed herewith is incorporated by reference herein in its entirety.

The invention claimed is:

1. A compound of general formula (I),

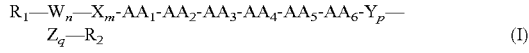

$$R_1\text{—}W_n\text{—}X_m\text{-}AA_1\text{-}AA_2\text{-}AA_3\text{-}AA_4\text{-}AA_5\text{-}AA_6\text{-}Y_p\text{—}Z_q\text{—}R_2 \quad (I)$$

its stereoisomers, mixtures thereof and/or its cosmetically or pharmaceutically acceptable salts, wherein:

$AA_1$ is selected from the group consisting of -Ser- and a bond;

$AA_2$ is selected from the group consisting of -Val- and -Ala-;

$AA_3$ is selected from the group consisting of -Arg- and -Thr-;

$AA_4$ is -Asn-;

$AA_5$ is selected from the group consisting of -Ala- and -Thr-;

$AA_6$ is selected from the group consisting of -Val- and a bond;

W, X, Y, Z are amino acids and are independently selected from amongst themselves;

n, m, p and q are independently selected from amongst themselves and have a value of 0 or 1;

n+m+p+q is smaller than or equal to 2;

with the condition that if $AA_1$ is a bond, $AA_2$ is -Val-, $AA_3$ is -Thr-, $AA_4$ is -Asn-, and $AA_6$ is -Val-, then $AA_5$ is -Ala-;

with the condition that if $AA_1$ is a bond, $AA_2$ is -Val-, $AA_3$ is -Thr-, $AA_4$ is -Asn-, $AA_5$ is -Ala- and $AA_6$ is a bond, then n+m+p+q is equal to 0;

with the condition that if $AA_1$ is a bond, $AA_2$ is -Ala-, $AA_3$ is -Thr-, $AA_4$ is -Asn-, $AA_5$ is -Thr- and $AA_6$ is a bond, then n+m+p+q is smaller than or equal to 1;

with the condition that if $AA_1$ is a bond, $AA_2$ is -Ala-, $AA_3$ is -Thr-, $AA_4$ is -Asn-, $AA_6$ is a bond, X is -Gly- and W is -Leu-, then $AA_5$ is -Thr-;

$R_1$ is selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl, and $R_5$—CO—, wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl;

$R_2$ is selected from the group consisting of —$NR_3R_4$, —$OR_3$, and —$SR_3$, wherein $R_3$ and $R_4$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl;

at least one of:
R₁ is not H, and
R₂ is not OH; and
R₁ and R₂ are not α-amino acids.

2. The compound according to claim 1, wherein R₁ is selected from the group consisting of H, a polymer derived from polyethylene glycol, and R₅—CO—, wherein R₅ is selected from the group consisting of substituted or unsubstituted $C_1$-$C_{24}$ alkyl radicals, substituted or unsubstituted $C_2$-$C_{24}$ alkenyls, substituted or unsubstituted $C_2$-$C_{24}$ alkynyls, substituted or unsubstituted $C_3$-$C_{24}$ cycloalkyls, substituted or unsubstituted $C_5$-$C_{24}$ cycloalkenyls, substituted or unsubstituted $C_8$-$C_{24}$ cycloalkynyls, substituted or unsubstituted $C_6$-$C_{30}$ aryls, substituted or unsubstituted $C_7$-$C_{24}$ aralkyl, substituted or unsubstituted heterocyclyl rings of 3-10 members, and substituted or unsubstituted heteroarylalkyls of 2 to 24 carbon atoms and 1 to 3 atoms other than carbon and an alkyl chain of 1 to 6 carbon atoms, and R₅—CO— is not an α-amino acid.

3. The compound according to claim 2, wherein R₁ is selected from the group consisting of H, acetyl, tert-butanoyl, hexanoyl, 2-methylhexanoyl, cyclohexanecarboxyl, octanoyl, decanoyl, lauroyl, myristoyl, palmitoyl, stearoyl, oleoyl, and linoleoyl.

4. The compound according to claim 1, wherein R₂ is selected from the group consisting of —NR₃R₄, —OR₃, —SR₃, wherein R₃ and R₄ are independently selected from the group consisting of H, a polymer derived from polyethylene glycol, substituted or unsubstituted $C_1$-$C_{24}$ alkyls, substituted or unsubstituted $C_2$-$C_{24}$ alkenyls, substituted or unsubstituted $C_2$-$C_{24}$ alkynyls, substituted or unsubstituted $C_3$-$C_{24}$ cycloalkyls, substituted or unsubstituted $C_5$-$C_{24}$ cycloalkenyls, substituted or unsubstituted $C_8$-$C_{24}$ cycloalkynyls, substituted or unsubstituted $C_6$-$C_{30}$aryls, substituted or unsubstituted $C_7$-$C_{24}$ aralkyls, substituted or unsubstituted heterocyclyl rings of 3-10 members, and substituted or unsubstituted heteroarylalkyl of 2 to 24 carbon atoms and 1 to 3 atoms other than carbon where the alkyl chain is of 1 to 6 carbon atoms and where —NR₃R₄ is not an α-amino acid.

5. The compound according to claim 4, wherein R₃ and R₄ are independently selected from the group consisting of H, methyl, ethyl, hexyl, dodecyl and hexadecyl.

6. The compound according to claim 1, wherein R₁ is selected from the group consisting of acetyl, lauroyl, myristoyl and palmitoyl.

7. A compound of general formula (I),

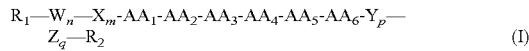

its stereoisomers, mixtures thereof and/or its cosmetically or pharmaceutically acceptable salts, wherein:
AA₁ is a bond;
AA₂ is -Ala-;
AA₃ is -Thr-;
AA₄-Asn-;
AA₅ is -Thr-;
AA₆ is a bond;
W, X, Y, Z are amino acids and are independently selected from amongst themselves;
n, m, p and q are independently selected from amongst themselves and have a value of 0 or 1;
n+m+p+q is smaller than or equal to 2;
R₁ is selected from the group consisting of acetyl, lauroyl, myristoyl and palmitoyl;

R₂ is selected from the group consisting of —NR₃R₄ and —OR₃, wherein R₃ and R₄ are independently selected from H, methyl, ethyl, hexyl, dodecyl and hexadecyl; and
R₁ and R₂ are not α-amino acids.

8. A cosmetic or pharmaceutical composition which comprises a cosmetically or pharmaceutically effective amount of at least one compound of general formula (I), its stereoisomers, mixtures thereof and/or its cosmetically or pharmaceutically acceptable salts, according to claim 1, and at least one cosmetically or pharmaceutically acceptable excipient or adjuvant.

9. The composition according to claim 8, wherein the compound of general formula (I), its stereoisomers, mixtures thereof and/or its cosmetically or pharmaceutically acceptable salts, is incorporated into a cosmetic or pharmaceutical delivery system or sustained release system selected from the group consisting of liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, liposheres, microemulsions, nanoemulsions, miniparticles, milliparticles, microparticles, nanoparticles and solid lipid nanoparticles or is adsorbed on a cosmetically or pharmaceutically acceptable solid organic polymer or solid mineral support selected from the group consisting of talc, bentonite, silica, starch and maltodextrin.

10. The composition according to claim 8, wherein the composition is present in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, elixirs, polysaccharide films, jellies and gelatin or is incorporated into a product selected from the group consisting of under-eye concealers, make-up foundation, make-up removing lotions, make-up removing milks, eye shadows, lipsticks, lip gloss, lip protectors and powders.

11. The composition according to claim 8, wherein the compound of general formula (I), its stereoisomers, mixtures thereof and/or its cosmetically or pharmaceutically acceptable salts, is incorporated into a fabric, a non-woven fabric or a medical device.

12. The composition according to claim 8, comprising a cosmetically or pharmaceutically effective amount of at least one adjuvant selected from the group consisting of agents which inhibit the release of cytokines, agents inhibiting matrix metalloproteinases, whitening or depigmenting agents, melanin synthesis inhibiting agents, anti-inflammatory and/or analgesic agents, anti-itching agents, antiangiogenic agents, anti-reddening agents, agents that inhibit vascular permeability, venotonic agents, agents acting on capillary circulation and/or microcirculation, calming agents, sunscreens and organic or mineral photoprotective agents active against ultraviolet A and/or B rays and/or infrared A rays, agents that inhibit serine proteases, agents stimulating melanocyte proliferation, agents for the treatment and/or care of sensitive skin, agents modulating PPARγ, agents inhibiting neuronal exocytosis, agents inhibiting muscular contraction, antiaging agents, anti-wrinkle agents, antiperspirant agents, anesthetic agents, inhibitors of acetylcholine-receptor aggregation, anti-cholinergic agents, melanin synthesis stimulating agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, AQP-3 modulating agents, aquaporin synthesis-modulating agents, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents stimulating the synthesis of lipids and components of the stratum corneum, ceramides, fatty acids, agents that inhibit collagen degradation, agents that inhibit elastin degradation, agents stimulating fibroblast proliferation, agents stimulating keratinocyte proliferation, agents stimulating adipocyte proliferation, agents stimulating keratinocyte differentiation, agents stimulating or delaying adipocyte differentiation, agents inhibiting acetylcholinesterase, skin relaxant agents, antihyperkeratosis agents, comedolytic agents, anti-psoriatic agents, DNA repair agents, DNA protecting agents, stabilizers, firming agents, anti-stretch mark agents, binding agents, agents regulating sebum production, lipolytic agents or agents stimulating lipolysis, adipogenic agents, agents modulating PGC-1α synthesis, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents stimulating angiogenesis, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor masking deodorants, chelating agents, plant extracts, essential oils, marine extracts, agents obtained from a biotechnological process, mineral salts, cell extracts, or mixtures thereof.

13. A compound of general formula (I),

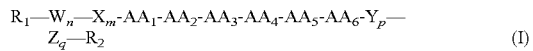

(I)

its stereoisomers, mixtures thereof and/or its cosmetically or pharmaceutically acceptable salts, wherein:

$AA_1$ is selected from the group consisting of -Ser- and a bond;

$AA_2$ is selected from the group consisting of -Val- and -Ala-;

$AA_3$ is selected from the group consisting of -Arg- and -Thr-;

$AA_4$ is selected from the group consisting of -Val- and -Asn-;

$AA_5$ is selected from the group consisting of -Ala- and -Thr-;

$AA_6$ is selected from the group consisting of -Val- and a bond;

W, X, Y, Z are amino acids and are independently selected from amongst themselves;

n, m, p and q are independently selected from amongst themselves and have a value of 0 or 1;

n+m+p+q is smaller than or equal to 2;

with the condition that if $AA_1$ is a bond, $AA_2$ is -Ala-, $AA_4$ is -Val- and $AA_6$ is a bond, then $AA_5$ is -Thr-;

with the condition that if $AA_1$ is a bond, $AA_2$ is -Val-, $AA_3$ is -Thr-, $AA_4$ is -Val- and $AA_6$ is a bond, then $AA_5$ is -Ala-;

with the condition that if $AA_1$ is a bond, $AA_2$ is -Val-, $AA_3$ is -Thr-, $AA_4$ is -Asn-, and $AA_6$ is -Val-, then $AA_5$ is -Ala-;

with the condition that if $AA_1$ is a bond, $AA_2$ is -Val-, $AA_3$ is -Arg-, $AA_4$ is -Val-, and $AA_6$ is -Val-, then $AA_5$ is -Thr-;

with the condition that if $AA_1$ is a bond, $AA_2$ is -Val-, $AA_3$ is -Thr-, $AA_4$ is -Asn-, $AA_5$ is -Ala- and $AA_6$ is a bond, then n+m+p+q is equal to 0;

with the condition that if $AA_1$ is a bond, $AA_2$ is -Ala-, $AA_3$ is -Thr-, $AA_4$ is -Val-, $AA_6$ is a bond and p+q is greater or equal to 1, then $AA_5$ is -Ala-;

with the condition that if $AA_1$ is a bond, $AA_2$ is -Ala-, $AA_3$ is -Thr-, $AA_4$ is -Asn-, $AA_5$ is -Thr- and $AA_6$ is a bond, then n+m+p+q is smaller than or equal to 1;

with the condition that if $AA_1$ is a bond, $AA_2$ is -Ala-, $AA_3$ is -Thr-, $AA_4$ is -Asn-, $AA_6$ is a bond, X is -Gly- and W is -Leu-, then $AA_5$ is -Thr-;

with the condition that if $AA_1$ is a bond, $AA_2$ is -Val-, $AA_3$ is -Thr-, $AA_4$ is -Val-, $AA_5$ is -Ala-, and $AA_6$ is a bond, then p and q are 0;

with the condition that if $AA_1$ is a bond, $AA_2$ is -Ala-, $AA_3$ is -Arg-, $AA_4$ is -Val-, $AA_6$ is a bond, Y is -Ala-, and Z is -Leu-, then $AA_5$ is -Ala-;

$R_1$ is selected from the group consisting of a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl, and $R_5$—CO—, wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl;

$R_2$ is selected from the group consisting of —$NR_3R_4$, —$OR_3$, and —$SR_3$, wherein $R_3$ and $R_4$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids.

14. The compound of claim 13 wherein: $AA_1$ is -Ser-; $AA_2$ is -Val-; $AA_3$ is -Arg-; $AA_4$ is -Val-; $AA_5$ is -Ala-; and $AA_6$ is -Val-.

15. A cosmetic or pharmaceutical composition which comprises:
a) a cosmetically or pharmaceutically effective amount of at least one compound of general formula (I),

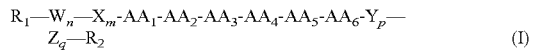
(I)

its stereoisomers, mixtures thereof and/or its cosmetically or pharmaceutically acceptable salts, wherein:
$AA_1$ is selected from the group consisting of -Ser- and a bond;
$AA_2$ is selected from the group consisting of -Val- and -Ala-;
$AA_3$ is selected from the group consisting of -Arg- and -Thr-;
$AA_4$ is selected from the group consisting of -Val- and -Asn-;
$AA_5$ is selected from the group consisting of -Ala- and -Thr-;
$AA_6$ is selected from the group consisting of -Val- and a bond;
W, X, Y, Z are amino acids and are independently selected from amongst themselves;
n, m, p and q are independently selected from amongst themselves and have a value of 0 or 1;
n+m+p+q is smaller than or equal to 2;
with the condition that if $AA_1$ is a bond, $AA_2$ is -Ala-, $AA_4$ is -Val- and $AA_6$ is a bond, then $AA_5$ is -Thr-;
with the condition that if $AA_1$ is a bond, $AA_2$ is -Val-, $AA_3$ is -Thr-, $AA_4$ is -Val- and $AA_6$ is a bond, then $AA_5$ is -Ala-;
with the condition that if $AA_1$ is a bond, $AA_2$ is -Val-, $AA_3$ is -Thr-, $AA_4$ is -Asn-, and $AA_6$ is -Val-, then $AA_5$ is -Ala-;
with the condition that if $AA_1$ is a bond, $AA_2$ is -Val-, $AA_3$ is -Arg-, $AA_4$ is -Val-, and $AA_6$ is -Val-, then $AA_5$ is -Thr-;
with the condition that if $AA_1$ is a bond, $AA_2$ is -Val-, $AA_3$ is -Thr-, $AA_4$ is -Asn-, $AA_5$ is -Ala- and $AA_6$ is a bond, then n+m+p+q is equal to 0;
with the condition that if $AA_1$ is a bond, $AA_2$ is -Ala-, $AA_3$ is -Thr-, $AA_4$ is -Val-, $AA_6$ is a bond and p+q is greater or equal to 1, then $AA_5$ is -Ala-;
with the condition that if $AA_1$ is a bond, $AA_2$ is -Ala-, $AA_3$ is -Thr-, $AA_4$ is -Asn-, $AA_5$ is -Thr- and $AA_6$ is a bond, then n+m+p+q is smaller than or equal to 1;
with the condition that if $AA_1$ is a bond, $AA_2$ is -Ala-, $AA_3$ is -Thr-, $AA_4$ is -Asn-, $AA_6$ is a bond, X is -Gly- and W is -Leu-, then $AA_5$ is -Thr-;
with the condition that if $AA_1$ is a bond, $AA_2$ is -Val-, $AA_3$ is -Thr-, $AA_4$ is -Val-, $AA_5$ is -Ala-, and $AA_6$ is a bond, then p and q are 0;
with the condition that if $AA_1$ is a bond, $AA_2$ is -Ala-, $AA_3$ is -Arg-, $AA_4$ is -Val-, $AA_6$ is a bond, Y is -Ala-, and Z is -Leu-, then $AA_5$ is -Ala-;
$R_1$ is selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl, and $R_5$—CO—, wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl;
$R_2$ is selected from the group consisting of —$NR_3R_4$, —$OR_3$, and —$SR_3$, wherein $R_3$ and $R_4$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl; and
at least one of:
$R_1$ is not H, and
$R_2$ is not OH; and
$R_1$ and $R_2$ are not α-amino acids; and
b) wherein the composition is present in a formulation selected from the group consisting of creams, multiple emulsions, anhydrous compositions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, emulsions, syrups, elixirs, polysaccharide films, jellies and gelatin.

* * * * *